United States Patent [19]
Raso et al.

[11] Patent Number: 6,140,091
[45] Date of Patent: Oct. 31, 2000

[54] ANTI-IDIOTYPE VACCINES TO ELICIT CATALYTIC ANTIBODIES

[75] Inventors: Victor Raso; Henry Paulus, both of Boston, Mass.

[73] Assignee: Boston Biomedical Research Institute, Watertown, Mass.

[21] Appl. No.: 09/102,451

[22] Filed: Jun. 22, 1998

Related U.S. Application Data

[60] Provisional application No. 60/050,388, Jun. 20, 1997.

[51] Int. Cl.[7] ........................................................ C12N 9/00
[52] U.S. Cl. ........................................................ 435/188.5
[58] Field of Search ........................................ 435/188.5

[56] References Cited

PUBLICATIONS

Lerner et al., *Science* 252: 659–667 (1991).
Benkovic, S.J., *Annu. Rev. Biochem.* 61: 29–54 (1992).
Izadyar et al., *PNAS USA* 90: 8876–8880 (1993).
Okuda et al., *AIDS Research & Human Retroviruses* 11: 933–943 (1995).
Stewart and Benkovic, *Nature* 375: 388–391 (1995).
Yang et al., *J. of the Amer. Chem. Society* 118: 5881 (1996).
Landry et al., *Science* 259: 1899 (1993).
Ghiara et al., *Science* 264: 82–85 (1994).
Pollack et al., *Science* 234: 1570–1573 (1986).
Avalle et al., *The FASEB Journal* 12: 1055–1060 (1998).
Friboulet, A., et al. (1994) App. Biochem. Biotechnol. 47, 229–239.
Avalle, B., et al. (1996) Ann. N.Y. Acad. Sci. 799, 172–175.
Hsu, K–H, et al. (1994) J. Agric. Food Chem. 42, 2343–2359.
Ban, N, et al. (1995) FASEB J. 9, 107–114.

*Primary Examiner*—Charles L. Patterson, Jr.
*Attorney, Agent, or Firm*—Kevin M. Farrell

[57] ABSTRACT

Disclosed are methods for the production of second generation catalytic antibodies. The disclosed methods offer a variety of advantages relative to prior art techniques. For example, the methods of the present invention do not require prior identification of the active site of an enzyme, the activity of which is desired in the catalytic antibody. Additionally, the disclosed methods enable the production of antibodies which catalyze chemical reactions which do not occur in nature.

9 Claims, 17 Drawing Sheets

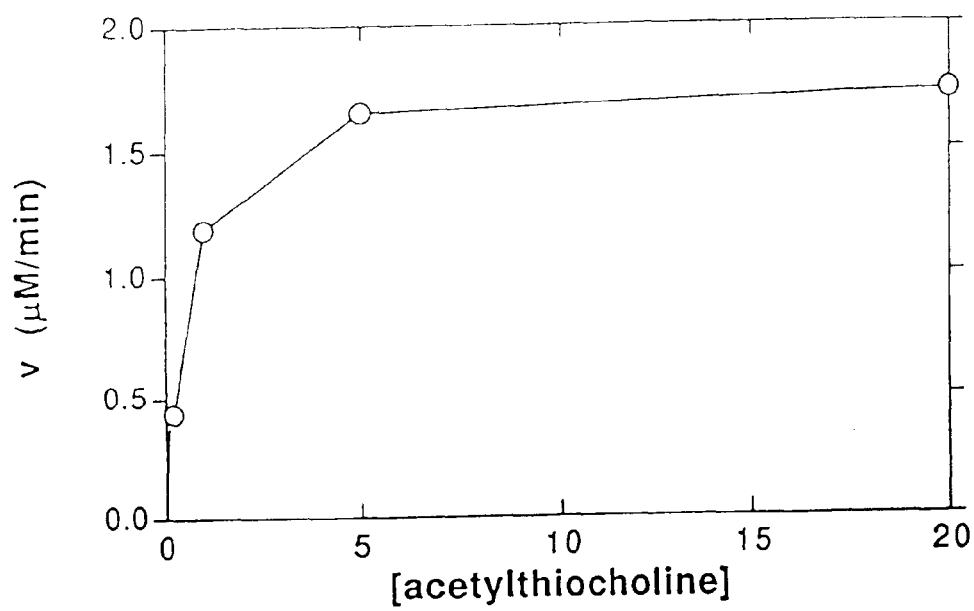
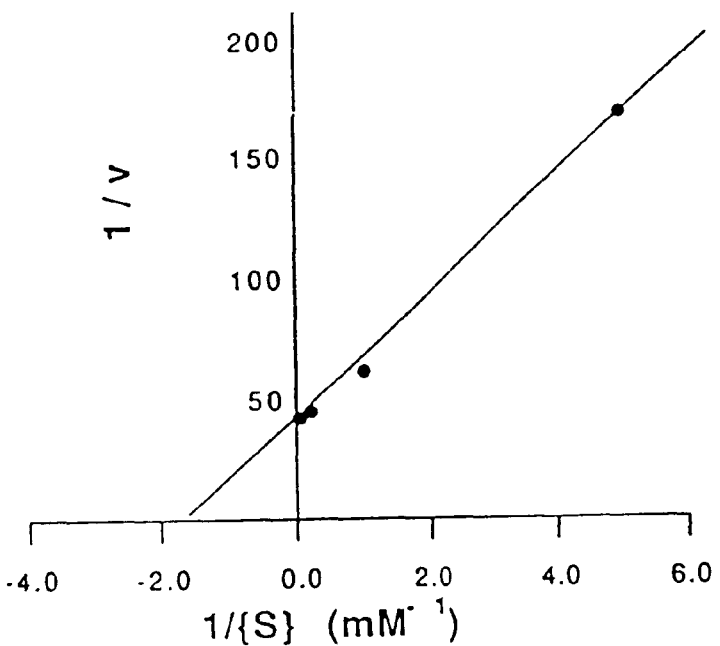
FIG. 7

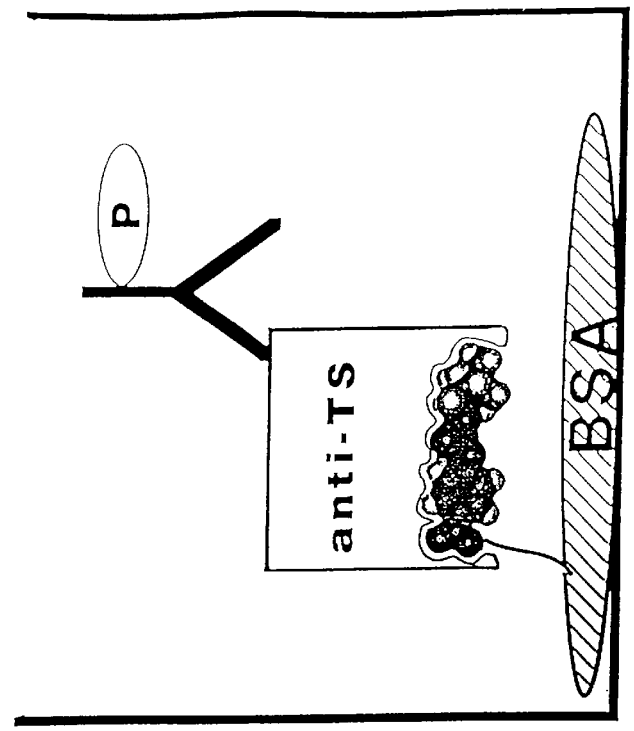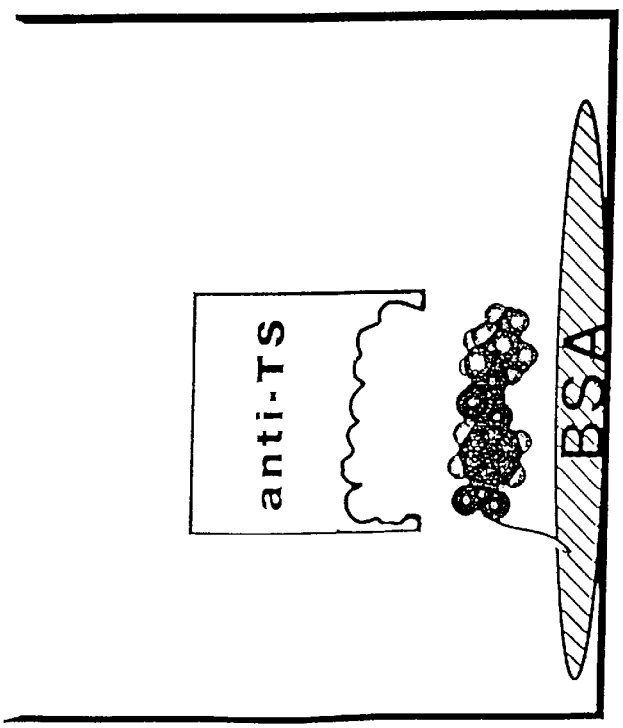
FIG. 9

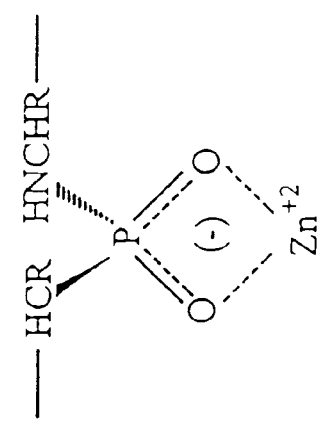
Phosphonamidate
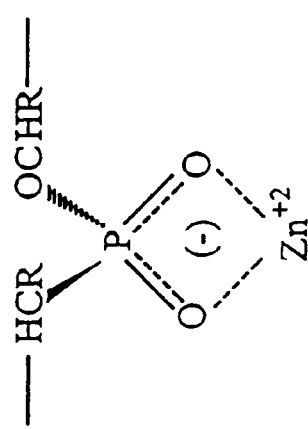
Phosphonate
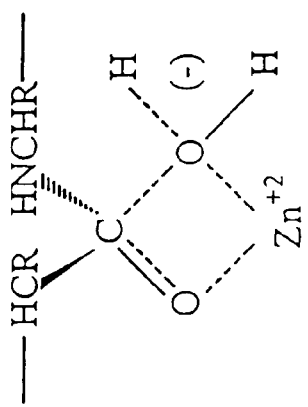
Transition-state
FIG. 10

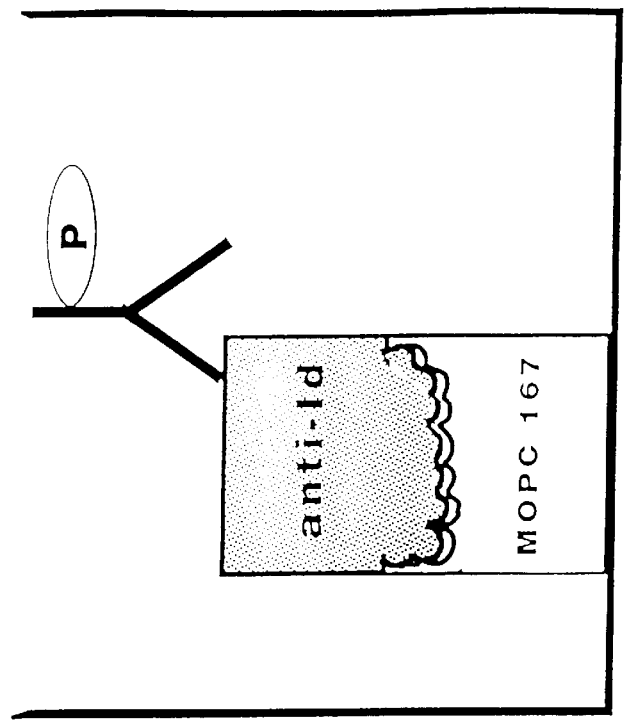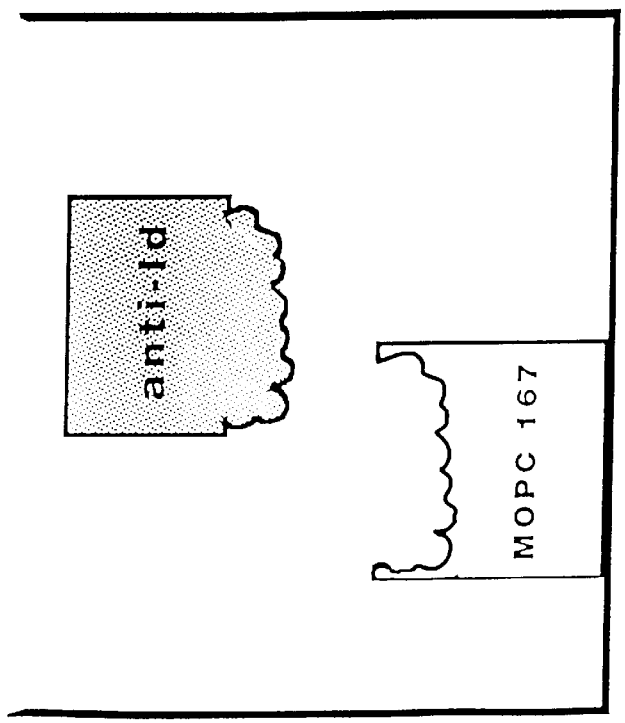
FIG. 16

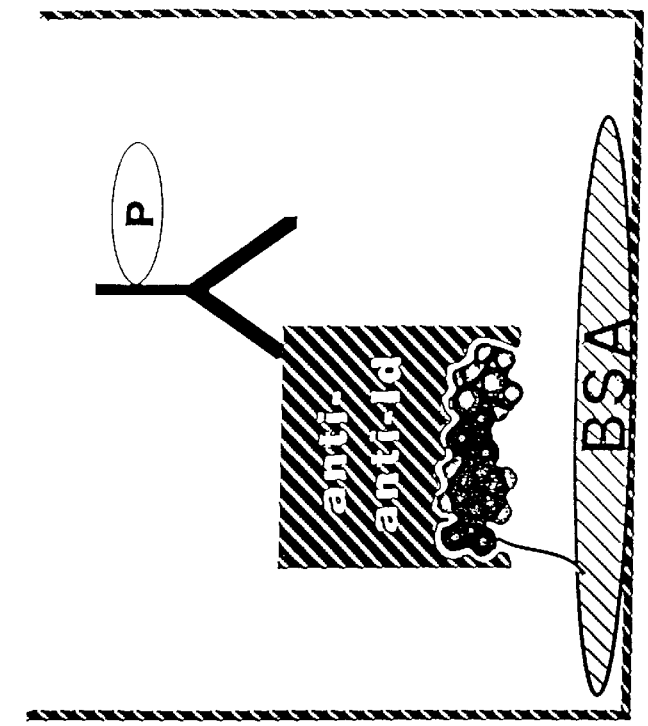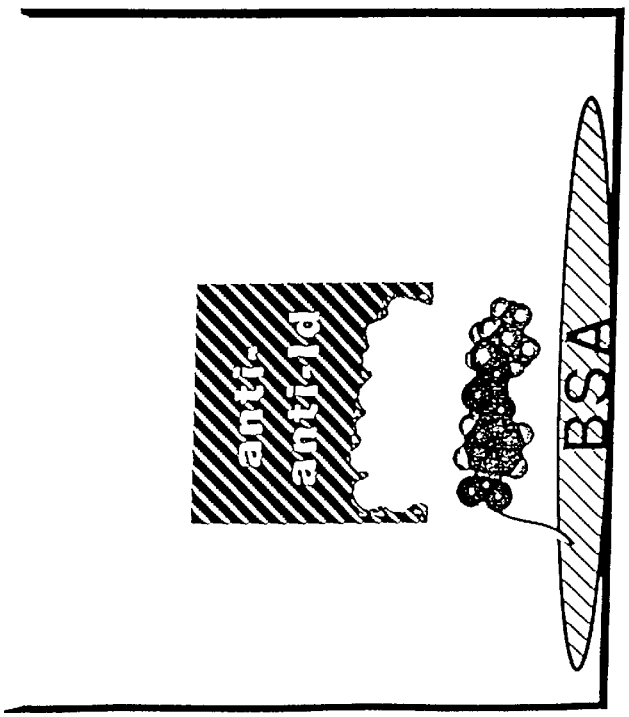
FIG. 17

ANTI-IDIOTYPE VACCINES TO ELICIT CATALYTIC ANTIBODIES

This application claims the benefit of U.S. Provisional Ser. No. 60/050,388 filed Jun. 20, 1997.

BACKGROUND OF THE INVENTION

More than 20 years ago, Raso and Stollar published the first formal study expressly aimed at inducing antibodies possessing catalytic activity (Raso and Stollar, *Biochemistry* 14: 591–599 (1975), Raso and Stollar, *J. Amer Chem Soc* 95: 1621 (1973), Raso and Stollar, *Biochemistry* 14: 584–591 (1975)). A transition state enzyme inhibitor was designed, synthesized and used as a hapten to elicit complementary antibody combining sites that would mimic the chosen enzyme active site. A fivefold rate enhancement was achieved for the tyrosine transamination reaction occurring at these antibody sites versus free in solution. This modest acceleration is actually quite significant considering that this result was obtained well before the development of hybridoma technology, so that only heterogeneous populations of affinity-purified rabbit serum antibodies could be used. Thus, the action of a small fraction of catalytic antibodies would have been largely offset by an excess of normal, binding antibodies competing by non-productively sequestering the reactants.

With the emergence of monoclonal antibody techniques, the field of catalytic antibodies has exploded, largely due to recent efforts from the laboratories of Lerner, Benkovic and Schultz (Lerner et al., *Science* 252: 659–667 (1991)). Homogeneous catalytic antibodies can now be selected, purified and studied in the absence of any competing non-catalytic species. Numerous catalytic antibodies, accelerating a large array of diverse chemical reactions, have been produced within the last several years. In light of the rapid progress since the early pioneering work, it is apparent that the time is now ripe to apply this unique technology to the pressing health problems confronting medical scientists today. However, there are several obstacles which still must be overcome before catalytic antibodies can be realistically considered for general clinical use.

The standard approach for generating catalytic antibodies involves immunizing an animal with a stable analog of the transition state of the reaction to be catalyzed and screening for antibodies that, like enzymes, bind more strongly to the transition state analog than to the corresponding substrate. Like enzymes, those select antibodies have a combining site that is complementary to the 3-D and ionic structure of the transition state analog. In a typical experiment, about half of the monoclonal antibodies raised in response to a transition state analog fall into the category. A small subclass (about 1%) of this category of antibodies actually catalyze the reaction of interest and can be identified by specific assay from among the candidates. Typically, the screening of 100–1,000 monoclonal antibodies will lead to one catalytic antibody.

The first-generation catalytic antibodies obtained in this manner are generally much less catalytically active than the corresponding naturally occurring enzymes. They generally display rate accelerations in the range of 500–300,000-fold while enzymes can provide rate enhancements on the order of $10^5$–$10^{10}$-fold over the uncatalyzed reaction. A main challenge therefore consists of engineering second-generation antibodies with higher catalytic efficiencies. Current approaches to this problem involve either chemical or genetic modification to introduce catalytic groups near the antigen combining site (Benkovic, S. J. *Annu. Rev. Biochem.* 61: 29–54 (1992)). These approaches depend on some knowledge of the active sites of analogous enzymes and must be applied individually to selected antibodies. This is a slow and labor-intensive process without guaranteed success, considering the low success rate of modifying the specificity or increasing the catalytic efficiency of natural enzymes.

Catalytic antibodies are particularly well suited as a novel treatment entity for cocaine addiction because they efficiently destroy the drug and nullify its stimulatory effect. Encouraging results have been obtained for the use of both conventional and catalytic anti-cocaine antibodies as a potential intervention to alleviate cocaine dependence (Yang et al., *Journal of the American Chemical Society* 118: 5881 (1996), Landry, D. W. J. A., *Scientific American* 276: 42 (1997), Landry et al., *Science* 259: 1899 (1993), Fox, B. S., *Drug Alcohol Depend* 48: 153 (1997), Fox et al., *Nat. Med.* 2: 1129 (1996), Landry et al., *J Addict Dis* 16: 1 (1997)). Presently, anti-cocaine catalytic antibodies are obtained by immunizing mice with a transition state analog antigen and then selecting those rare clones which have the appropriate hydrolytic activity. There are several obstacles which still must be overcome before anti-cocaine antibodies can be realistically considered for general clinical use. The use of murine catalytic antibodies will present problems for the treatment of humans with an addiction to drugs because, as foreign proteins, they will elicit an inhibitory immune response. Moreover, these primary catalytic antibodies obtained by current approaches are inadequate since they usually have very low catalytic activity. Furthermore, because of their transient action, it is unlikely that passively administered anti-cocaine antibodies would be effective for the chronic problem of repeated use, which characterizes drug addiction. These facts indicate the need to develop second generation anti-cocaine antibodies with improved catalytic activities that can be generated by the patients themselves.

BRIEF DESCRIPTION OF THE DRAWINGS

FIG. 7 Lineweaver-Burk plot for MOPC 167 catalyzed acetylthiocholine hydrolysis.

FIG. 9 Anti-transition state ELISA.

FIG. 10 Comparison of the transition state for peptide hydrolysis and its analogs.

FIG. 16 Anti-idiotype ELISA.

FIG. 17 Anti-anti-idiotype ELISA.

DETAILED DESCRIPTION OF THE INVENTION

The subject invention is based on the development of a new method for the production of second generation catalytic antibodies. The new method offers a variety of advantages. For example, unlike current techniques, the method of the present invention does not require prior identification of the active site the enzyme, the activity of which is desired in the catalytic antibody (Izadyar, L. et al., *PNAS* 772: 209–11 (1995)). Moreover, this technique allows one to develop antibodies that catalyze chemical reactions which do not occur in nature. Lastly, the method provides a method for generating catalytic antibody-eliciting vaccines which are usable in humans.

The method of the present invention involves 3 separate immunizations. In preferred embodiments, at least the first two immunizations are carried out in an experimental host from which hybridomas can be easily generated (e.g., mice). Alternatively, the first generation antibody may be produced by in vitro immunization or by screening of a combinatural immunoglobulin library. The immunogen employed in the first immunization step is designed following consideration of the chemical reaction which the second generation catalytic antibodies of the present invention is intended to catalyze. This phase of the experimental design requires consideration of substrate and product structure. In the conversion from substrate to product, an unstable transition state is formed. Following careful consideration of the substrate and product, one of skill in the art can design a stable molecule which resembles the transition state intermediate. This stable molecule which resembles the transition state intermediate is referred to herein as a transition state analog. For example, many transition state intermediates involved in hydrolytic reactions exhibit tetrahedral geometry in contrast to the planar geometry of the substrate. Using techniques routine in the art of organic synthesis, a transition state analog having similar atomic composition, configuration, and charge can be designed, which exhibits stable tetrahedral geometry. (Thompson, R. C., *Biochemistry* 12: 47–51 (1973), Wolfenden, R., *Annu. Rev. Biochem. Bioeng.* 5: 271–306 (1976), Bartlett and Marlowe, *Biochemistry* 22: 4618–24 (1983)).

Figure 1:
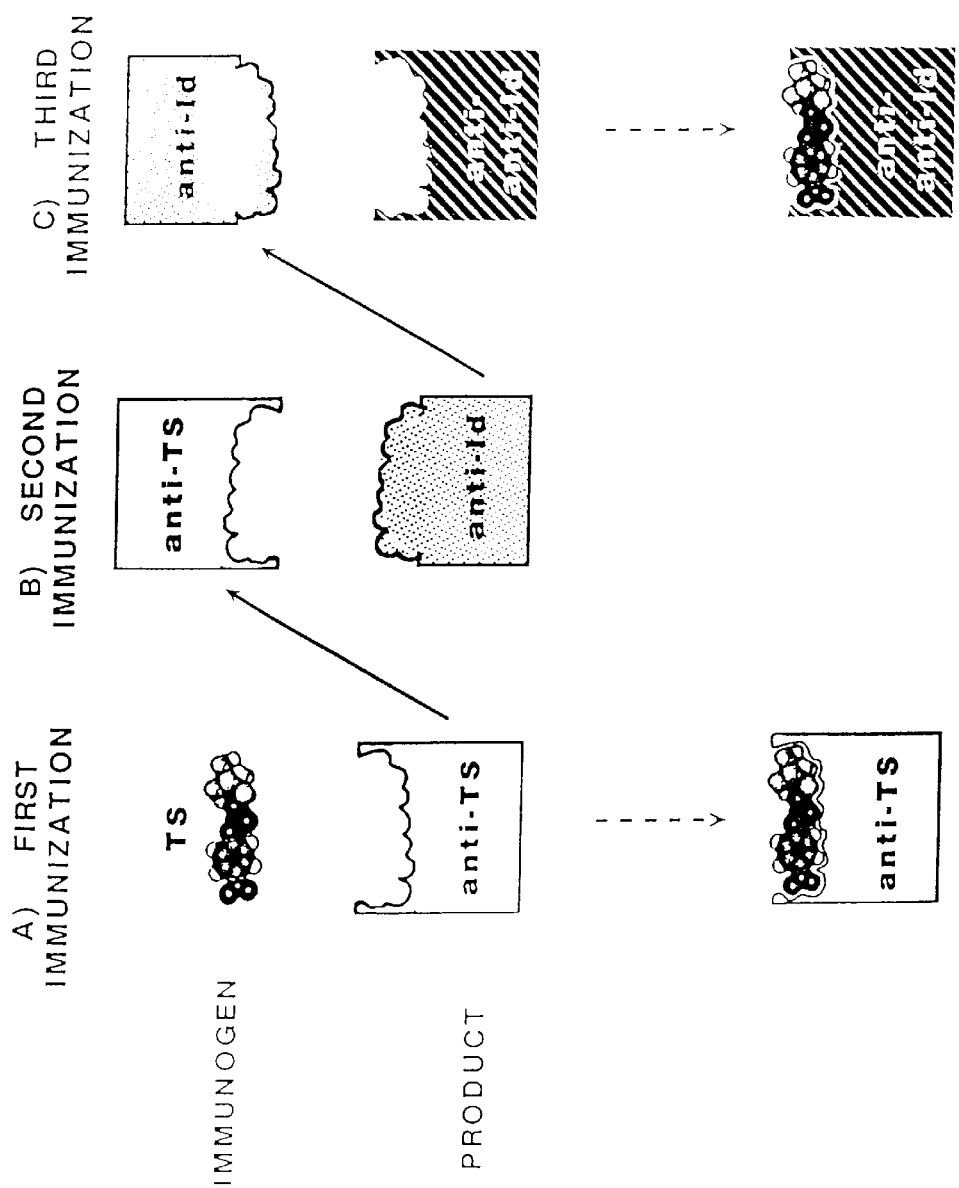
FIG. 1 Production of anti-anti-idiotype catalytic antibodies.

In the first immunization step, a transition state analog (TS) is used to immunize an animal (typically a mouse) by conventional techniques (FIG. 1A). In preferred embodiments, the transition state analog is linked to a carrier protein. Hybridomas are then produced by standard techniques using antibody producing cells from the animal. Alternatively, in vitro immunization may be used which does not require linking of the transition state analog to a carrier protein. Monoclonal antibodies produced by these hybridomas are then screened for a) binding specificity for the transition state analog; and b) catalytic activity (i.e., ability to convert substrate to product).

Catalytic monoclonal antibodies (anti-TS) identified in the screening procedure described above are then used to immunize a second animal (again, typically a mouse) by conventional techniques (FIG. 1B). This results in the production of cells which produce anti-idiotypic antibodies (anti-Id) which form an internal image of the combining site and thus have a structure which mimics the transition state (FIG. 1B). Hybridomas are made and the anti-idiotypic monoclonal antibodies produced by the hybridomas are screened in a dual elisa and by a variety of competitive assays. For example, the anti-idiotypic monoclonals are tested by a dual elisa designed to determine whether the anti-idiotypic monoclonals bind to the catalytic monoclonal antibody used as an immunogen in the second immunization, but not to a class and light chain matched control antibody with no catalytic activity.

Figure 2:
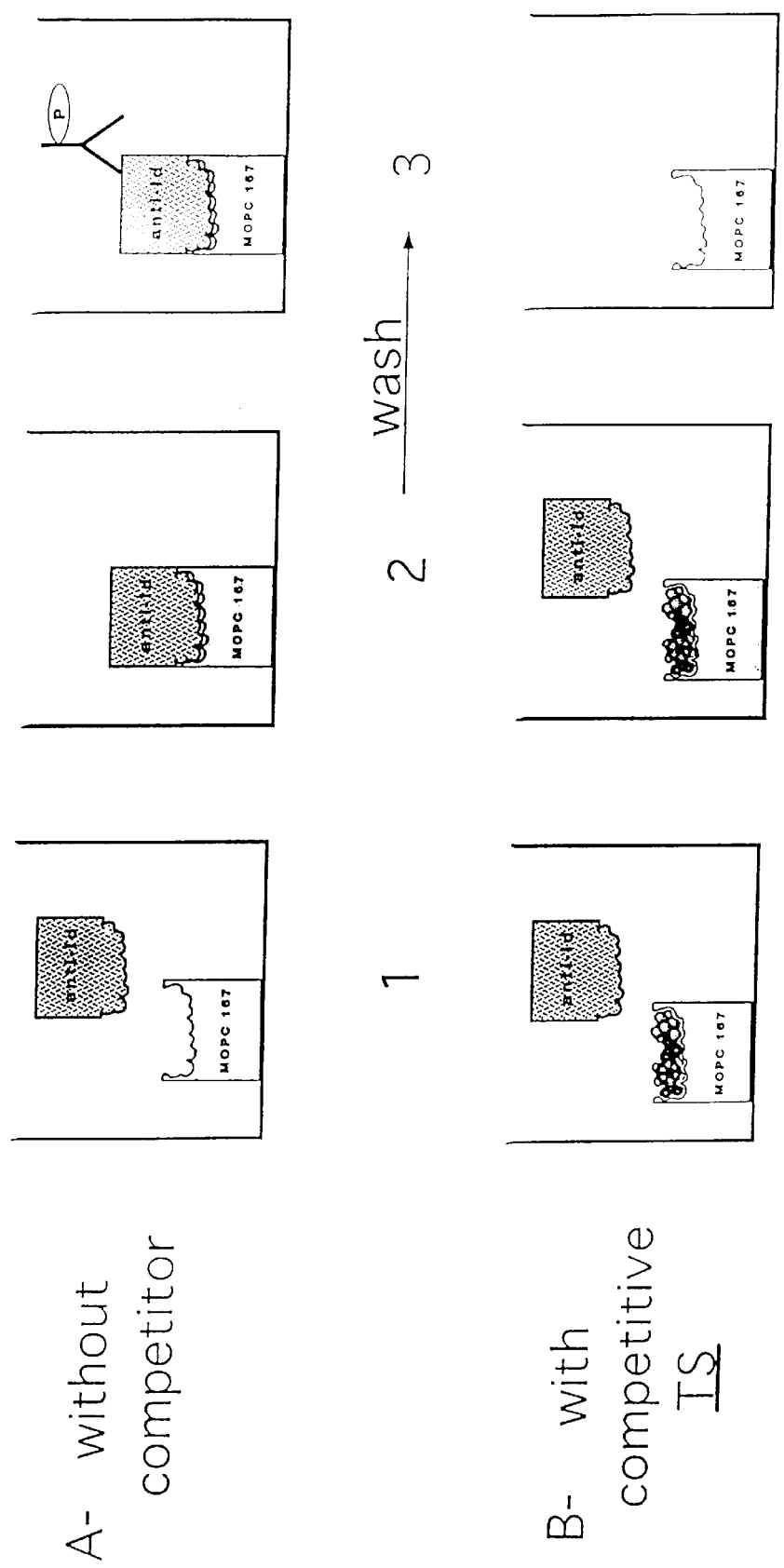
FIGS. 2A and 2B Site-specific competition between the transition state analog and anti-idiotype antibody.

A first screen involving competitive ELISA uses a free transition state analog to block binding (FIG. 2). In this assay, the catalytic antibody used as immunogen for the second immunization is attached to a solid support and the anti-idiotypic antibodies are allowed to bind to this antigen (FIG. 2A). An otherwise identical experiment is conducted in the presence of the transition state analog (FIG. 2B). If the monoclonal antibody product of the second immunization is, in fact, a true combining site-specific anti-idiotypic monoclonal antibody, its binding will be blocked by this transition state analog (FIG. 2B).

Figure 3:
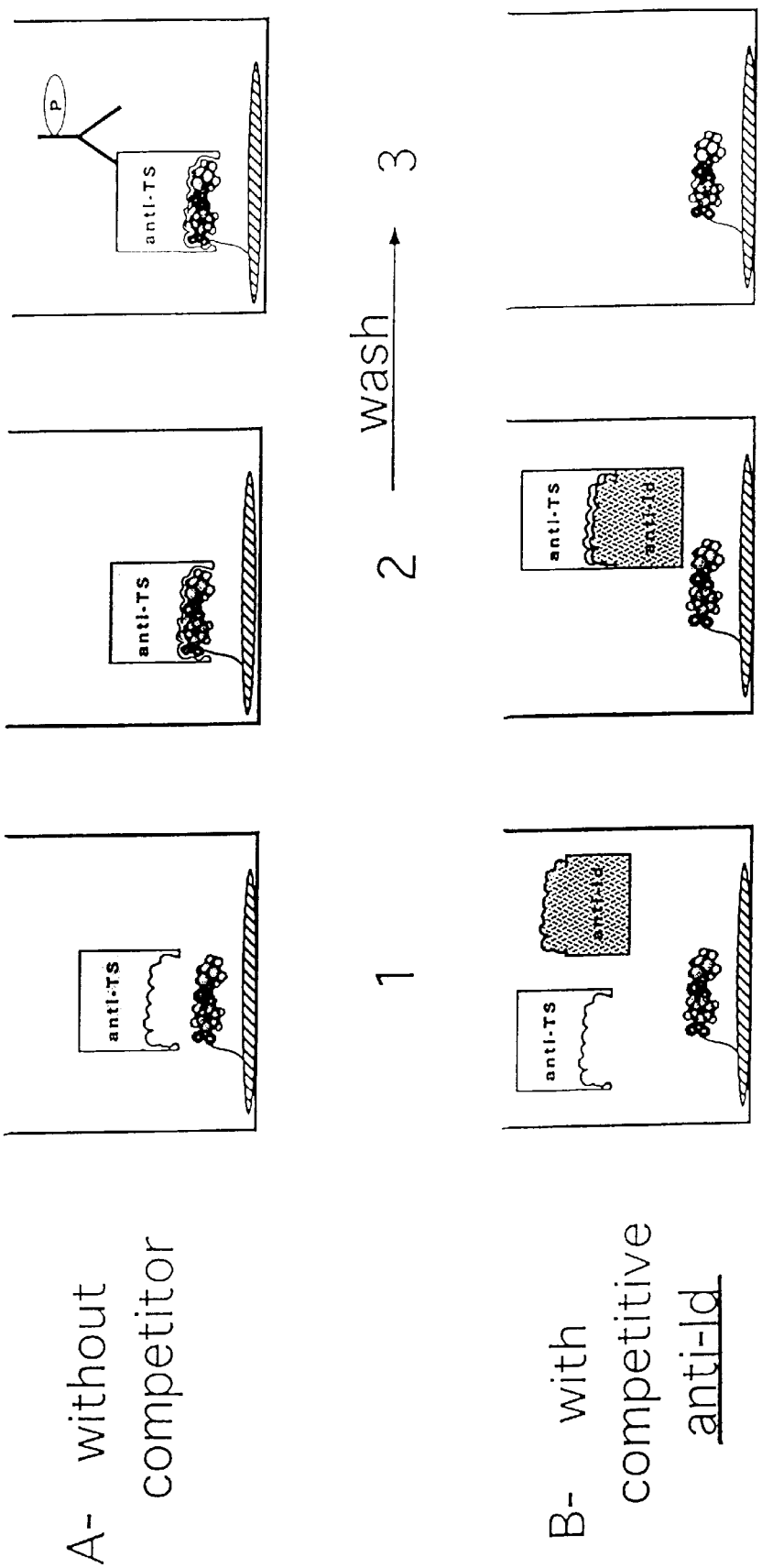
FIGS. 3A and 3B Competitive ELISA for site-specific interaction between anti-TS and anti-idiotype antibody.

In a second competitive screen (FIG. 3), a transition state analog-bovine serum albumin conjugate is attached to a solid support and the catalytic antibody hybridoma product of the first immunization is allowed to bind (FIG. 3A). An otherwise identical experiment is conducted in the presence of the monoclonal anti-idiotype antibody product of the second immunization (FIG. 3B). In the latter case, the anti-idiotypic monoclonal antibody blocks the binding site of the catalytic antibody and prevents it from binding to the transition state analog-bovine serum albumin conjugate on the plate (FIG. 3B). Optionally it can be demonstrated that the anti-idiotypic monoclonal antibody will prevent the catalytic antibody from catalyzing its reaction by virtue of binding to and blocking the catalytic active site.

In the third immunization (FIG. 1C), the anti-idiotypic monoclonal antibodies are used to immunize an animal to produce an anti-anti-idiotypic antibody (anti-anti-Id) having catalytic activity. In this immunization, the preferred format is active immunization and the animal to be immunized is a human. In the active format, the immunization is essentially a vaccination. Second generation catalytic antibodies are produced in vivo. Alternatively, an experimental host (e.g., a mouse) can be immunized as above and the resulting improved second generation catalytic antibodies can be isolated for use as passive therapeutic reagents. This anti-idiotype vaccine approach offers several important advantages. First, the availability of the gene facilitates mass production of anti-idiotype single chain Fv antibodies in bacteria. The anti-idiotype could also be humanized or could be of human origin so that only antibodies against the idiotype determinant would be elicited upon vaccination of humans. Expression of the idiotype determinant on a live attenuated virus or as part of a recombinant adjuvant protein would yield very active vaccines for inducing catalytic antibodies. Lastly, the anti-idiotype DNA itself could be used as a vaccine (Robinson et al., *Annals. of the New York Academy of Sciences* 772: 209–11 (1995), Okuda et al., *AIDS Research & Human Retroviruses* 11: 933–43 (1995)) to establish immunity by virtue of eliciting catalytic antibodies.

All immunizations are formulated in a manner consistent with well-established immunization protocols. It should be noted that the approach proposed here goes one step further than prior art methods in that catalytic antibodies are produced without the use of a naturally occurring enzyme. This difference is of crucial importance because it permits the preparation of catalytic antibodies with specificities that do not exist in nature.

Another basic advantage of the approach proposed here is its applicability to the in vivo generation of catalytic antibodies for therapeutic purposes, for instance, as antiviral agents. One example would be a vaccine approach to generate catalytic antibodies which hydrolyze the V3 loop of the HIV gp120 envelope protein. Catalytic antiviral antibodies offer a great advantage over conventional neutralizing antibodies because they permanently alter and inactivate the virus rather than merely transiently blocking the virus. The standard approach would be to immunize a patient with a chemically synthesized transition state analog coupled with an antigenic carrier to elicit catalytic antibodies which serve as proteases with the appropriate specificity. However, a much more powerful approach would be to prepare a first-generation catalytic antibody by the standard procedure in mice, as well as its anti-idiotypic antibody. The anti-idiotypic antibody could then be used as an immunogen for vaccination instead of the original V3 transition state analog. This anti-idiotype vaccine approach offers several important advantages. First, the availability of the gene facilitates mass production of anti-idiotype single chain Fv antibodies in bacteria. The anti-idiotype could also be humanized or could be of human origin so that only antibodies against the idiotype determinant would be elicited upon vaccination of humans. Expression of the idiotype determinant on a live attenuated virus or as part of a recombinant adjuvant protein would yield very active vaccines for inducing catalytic antibodies. Lastly, the anti-idiotype DNA itself could be used as a vaccine (Robinson et al., *Annals. of the New York Academy of Sciences* 772: 209–11 (1995), Okuda et al., *AIDS Research & Human Retroviruses* 11: 933–43 (1995)) to establish immunity to HIV by virtue of eliciting catalytic anti-V3 antibodies.

Since the combining site of an anti-idiotypic antibody is essentially an image of the original antigen it can serve as an analog of the original antigen to elicit second generation antibodies, anti-anti-idiotypic antibodies, which will bind the original antigen. If the original antigen is a transition state analog, anti-anti-idiotypic antibodies have as much chance of being catalytic antibodies as the first-generation anti-transition state antibodies. The key feature of this approach, however, is that anti-anti-idiotypic antibodies against first-generation catalytic antibodies will almost exclusively bind the transition state much more strongly than the substrate and will therefore be highly enriched in catalytic antibodies. This conclusion is based on the following considerations:

1) Because transition state intermediates are not stable chemical substances, transition state analogs are, by necessity, imperfect representations of the transition state and also incorporate features characteristic of the substrate that are necessary to assure binding specificity. Antibodies against transition state analogs therefore often bind the substrate and the transition state analog equally and even those binding the transition state analog preferentially may recognize a feature that is unique to the analog and does not occur in the true transition state. This explains the very low frequency of catalytic antibodies ($<10^{-3}$) among monoclonal antibodies raised against transition state analogs.
2) On the other hand, the combining site of the few first-generation catalytic antibodies found among the monoclonal antibodies obtained after immunization with transition state analogs preferentially, recognizes the true transition state of the reaction catalyzed, even if catalytic efficiency is relatively low (e.g., with rate enhancement as little as 1,000-fold over the spontaneous reaction rate). This follows because catalysis depends on the selective stabilization by the enzyme of the transition state; according to transition state theory (Stewart and Benkovic, *Nature* 375: 388–391 (1995)), a 1,000-fold rate enhancement translates into a 1,000-fold higher affinity for the transition state than for the substrate. The binding site of even a relatively weak catalytic antibody is thus a relatively good complement of the transition state.
3) The combining sites of anti-idiotypic antibodies raised in the same animal species (e.g. mouse) against a catalytic antibody, being complementary to the combining site of the catalytic antibody, which is in turn complementary to the transition state, is therefore an image of the transition state. Moreover, it is a more effective image of the transition state than the transition state analog used in the original immunization because it is representative of the true transition state that actually occurs in catalysis by the first-generation catalytic antibody. If used as an immunogen to raise anti-anti-idiotypic antibodies, the anti-idiotypic antibody should therefore give rise to second-generation catalytic antibodies, essentially all of which bind the true transition state more tightly than the substrate.
4) The fact that essentially all anti-anti-idiotypic antibodies will be transition state-specific makes them a potentially rich source of second-generation catalytic antibodies. Since each of these represent an independent immunoglobulin molecule, the second-generation catalytic antibodies constitute a broad repertoire of different antibodies from which catalytic antibodies with the desired properties can be selected. Indeed, their anticipated high frequency and diversity may lend itself to combinatorial screening approaches for selecting catalytic antibodies with the desired properties. The second-generation catalytic antibodies thus obtained may be suitable for the projected use or can be the starting material for the preparation of third-generation catalytic antibodies by a second cycle of anti-anti-idiotype selection or by conventional genetic or protein engineering approaches.

In another aspect, the current invention is related to a method for treatment of drug abuse that induces the production of endogenous catalytic antibodies directed at hydrolyzing cocaine in a therapeutically useful manner. More specifically, the invention relates to the use of an idiotype vaccine to obtain second-generation anti-cocaine catalytic antibodies in a human host. Like the previous strategy, this is based on the fact that the combining site of an anti-idiotypic antibody is essentially an image of the original antigen, illustrated schematically in FIG. 1. In preferred embodiments a mouse is immunized with a cocaine transition state (TS) analog (FIG. 1A) so that a monoclonal anti-cocaine transition state antibody with catalytic activity is obtained (anti-TS) (Yang et al., *Journal of the American Chemical Society* 118: 5881 (1996), Landry, D. W. J. A., *Scientific American* 276: 42 (1997), Landry et al., *Science* 259: 1899 (1993)). This anti-TS is used as an immunogen (FIG. 1B) to obtain an anti-idiotype which is a replica of the true cocaine transition state, TS. That anti-idiotype is then used as an antigen (FIG. 1C) instead of the original chemically synthesized cocaine TS analog, to obtain a catalytic anti-anti-idiotype with the desired cocaine hydrolytic activity. The induced catalytic antibodies will be much more effective than conventional neutralizing antibodies because they permanently alter and inactivate the drug rather than just transiently block its action. In the preferred embodiment, functional levels of catalytic antibodies would be maintained in the patient with occasional booster injections.

Alternative embodiments of the current invention offer additional benefits. The gene for an anti-idiotype sFv vaccine could be genetically engineered and mass produced in bacteria. Additionally, the anti-idiotype could also be humanized or could be of human origin so that only antibodies against the idiotype determinant would be elicited upon vaccination of humans. Alternately, expression of the idiotype determinant on a live attenuated virus or as part of an adjuvant recombinant protein would yield very active vaccines for inducing anti-cocaine catalytic antibodies. Lastly, the anti-idiotype DNA itself could be used as a vaccine (Robinson et al., *Annals of the New York Academy of Sciences* 772: 209 (1995), Okuda et al., *AIDS Research & Human Retroviruses* 11(8): 933 (1995)) to establish immunity to cocaine addiction by virtue of eliciting catalytic anti-cocaine antibodies.

EXEMPLIFICATION

Example 1

Production of First Generation Anti-Transition State Catalytic Antibodies

As an initial trial for generating anti-idiotype antibodies, it was decided to use the MOPC 167 catalytic antibody as an antigen. The cells which secrete the mouse myeloma catalytic antibody MOPC 167 were provided by Dr. Michael Potter. The IgA antibody was isolated from ascites fluid by affinity chromatography using the Sepharose-immobilized p-aminophenylphosphorylcholine transition state analog as previously described (Chesebro and Metzger, *Biochemistry* 11: 766–771 (1972). Fab fragments were prepared by pepsin digestion and purified by affinity chromatography. Both the antibody and Fab fragment migrated as expected when analyzed by PAGE under both reducing and non-reducing conditions. The Fab fragment gave an appropriate mass spectral peak at 48,423 kDa.

Figure 4:
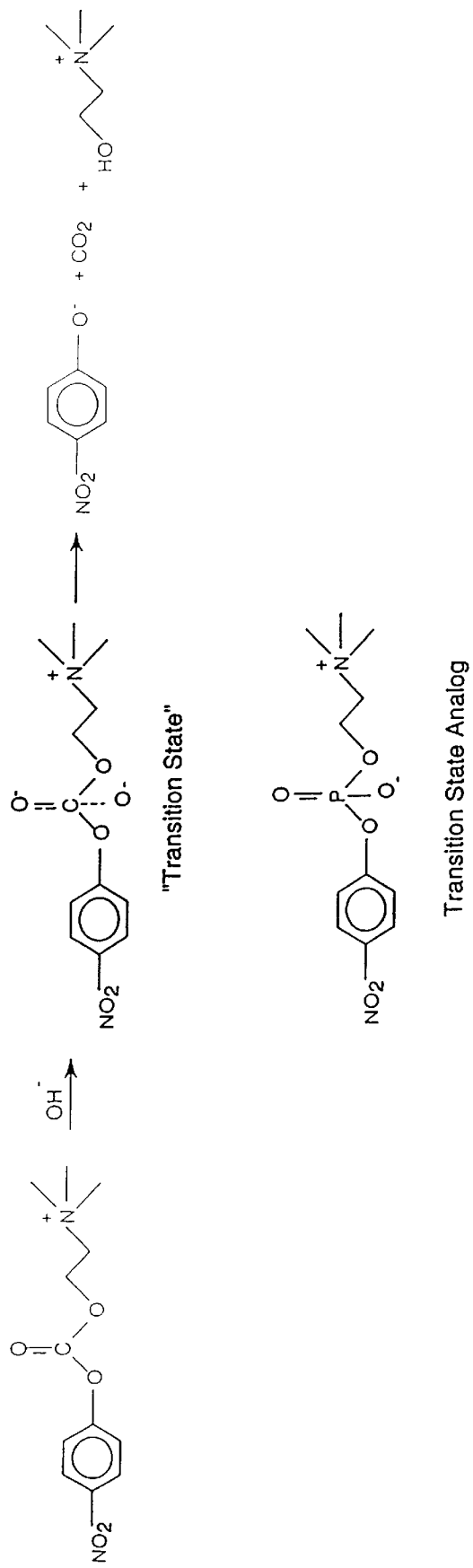
FIG. 4 Carbonate ester hydrolysis.

FIG. 4 illustrates the reaction catalyzed by MOPC 167, the putative transition state and the p-nitrophenylphosphorylcholine transition state analog according to (Pollack et al., *Science* 234: 1570–1573 (1986)). The substrate for measuring carbonate ester hydrolysis was synthesized using p-nitrophenol, phosgene and choline chloride. MOPC 167 was assayed by monitoring p-nitrophenol production at 400 nm and catalyzed the hydrolytic reaction (FIG. 4) as previously reported (Pollack et al., *Science* 234: 1570–1573 (1986)).

Figure 5:
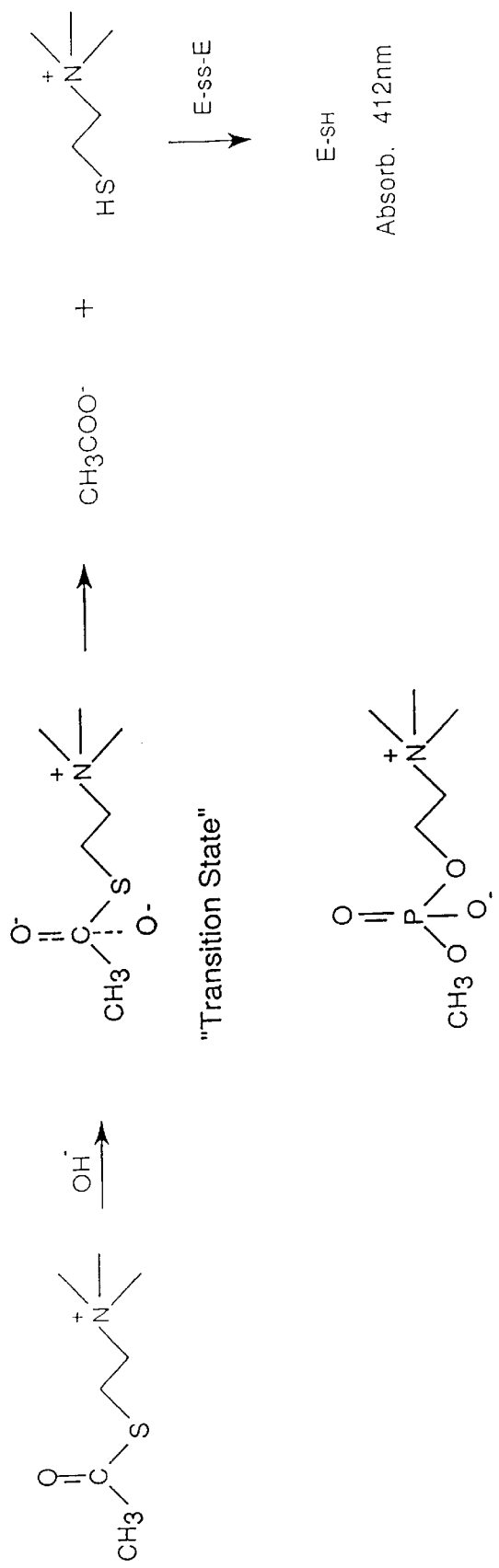
FIG. 5 Thioester hydrolysis.

It was recognized that the phosphocholine moiety might serve as a transition state analog for ester hydrolysis according to the scheme shown in FIG. 5. MOPC 167 was therefore tested for esterase activity using acetylthiocholine as a substrate and Ellman's reagent (E-ss-E) for the detection of thiol production (Izadyar et al., *Proceedings of the National Academy of Sciences of the United States of America* 90: 8876–80 (1993)).

Figure 6:
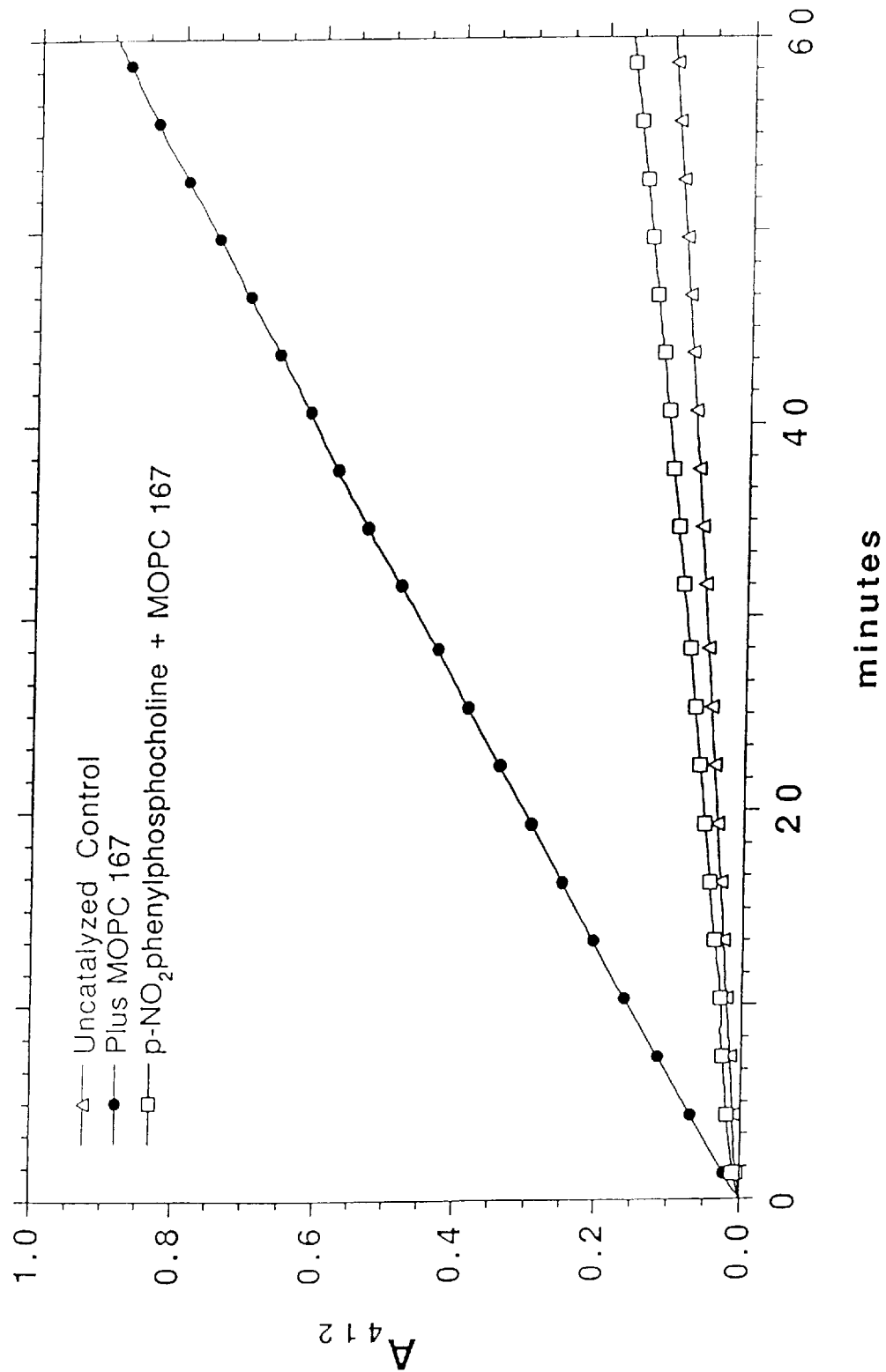
FIG. 6 Kinetics for acetylthiocholine hydrolysis catalyzed by MOPC 167.

The kinetics curves provided in FIG. 6 indicate that MOPC 167 does indeed possess this second, newly discovered activity. Importantly, the esterase activity was almost completely blocked by the inclusion of the non-cleavable p-nitrophenylphosphorylcholine transition state analog (FIG. 6) showing that catalysis is site-dependent. Analysis of the Lineweaver-Burk plot for MOPC 167 catalyzed acetylthiocholine hydrolysis (FIG. 7) gave a Michaelis constant, $k_m$=627 $\mu$M and catalytic constant, $k_{cat}$=0.25 min$^{-1}$ which were close to the values measured for carbonate ester hydrolysis (Pollack et al., *Science* 234: 1570–1573 (1986)). However, since spontaneous hydrolysis of this substrate is low, $k_{uncat}$=4×10$^{-5}$ min$^{-1}$, the $k_{cat}/k_{uncat}$=6,000 is about 10-fold greater than that recorded for MOPC 167 catalysis of the carbonate ester reaction. That rate enhancement should be increased by using idiotypic mimicry.

Figure 8:
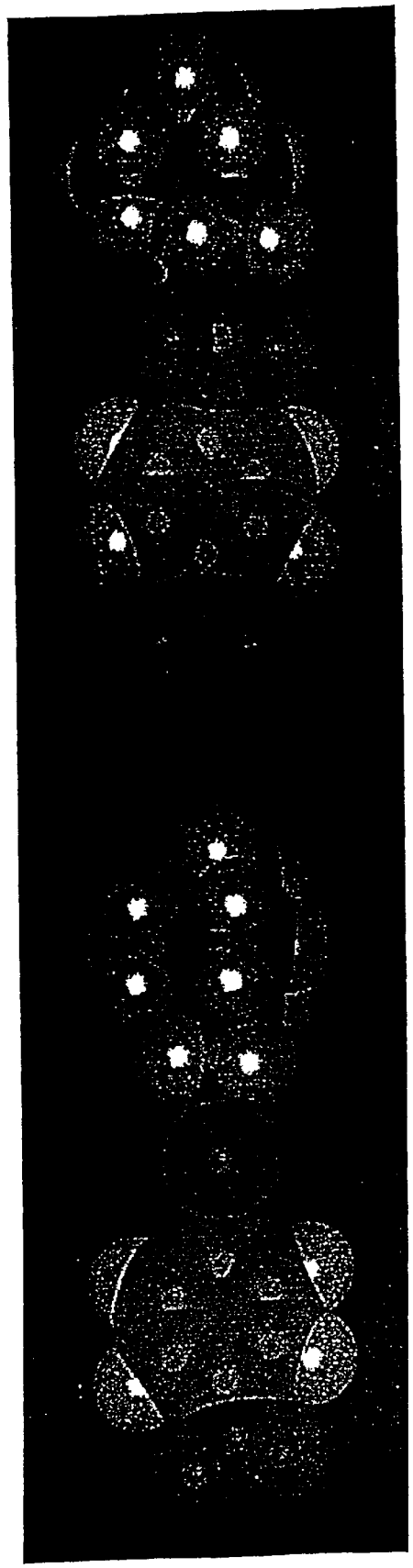
FIG. 8 Carbonate substrate $NO_2$—$C_6H_4$—O—CO—O—$C_2H_4$—$N^+$—$(CH_3)_3$ (left) versus the p-nitrophenylphosphorylcholine transition state $NO_2$—$C_6H_4$—O—$PO_2^-$—O—$C_2H_4N^+$—$(CH_3)_3$ (right).

In addition to the MOPC 167 myeloma antibody, it was decided to also generate several primary catalytic antibodies to use for the induction of anti-idiotype antibodies. The same p-nitrophenylphosphorylcholine transition state analog that binds to MOPC 167 was used as a hapten to elicit antibodies since the negative charge and tetrahedral geometry of the PO$^-_4$ group mimics the transition state to a greater extent then it resembles the planar CO$_3$ region of the substrate (FIGS. 4, 5 and 8).

The procedure for synthesizing the affinity matrix described above (Chesebro and Metzger, *Biochemistry* 11: 766–771 (1972)) involved reduction of the p-nitrophenylphosphorylcholine transition state analog to give a p-NH$_2$ derivative and then treatment with NaNO$_2$ to obtain the diazonium salt. Therefore, this reactive species was used to form a diazo linkage with both the KLH and BSA carrier proteins. After reaction, the diazotized proteins were dialyzed extensively.

Successful coupling of the transition state analog was verified by the red color produced and by specific binding of MOPC 167 (anti-TS) to these modified proteins as measured by ELISA using a peroxidase-labeled anti-mouse IgA reagent (FIG. 9). The transition state-KLH conjugate was emulsified in complete Freunds adjuvant and injected i.p. into BALB/c mice in order to generate catalytic antibodies that will bind the p-nitrophenylphosphorylcholine transition state and catalyze the reactions outlined in FIGS. 4 and 5. Sera and monoclonal antibodies obtained from these mice will be screened for anti-transition state antibodies by ELISA. This assay uses the diazophenylphosphorylcholine-BSA conjugate adsorbed to microtitre wells and a peroxidase-labeled anti-mouse IgG detection reagent (FIG. 9). These select antibodies will then be screened for an ability to catalyze carbonate ester and thioester hydrolysis using the substrates shown in FIGS. 4 and 5.

While it is relatively easy to obtain or generate catalytic antibodies with esterase activity, these antibodies and the anti-idiotypes generated by them would have no clinical application. However, another more long-term objective of the laboratory is to generate catalytic antibodies which will selectively cleave the gp120 envelope protein of HIV and others specific for the β-amyloid peptide implicated as the causative agent in Alzheimer's disease. Each antibody would permanently inactivate many target molecules rather than just acting stoichiometrically. When such catalytic antibodies become available, they too will be good candidates for eliciting anti-idiotype antibodies with clinical relevance. Substantial progress has already been achieved to this end.

Several transition state peptides that resemble the V3-loop of HIV-1 or the Alzheimer's β-amyloid peptide have been synthesized. They have a tetrahedral phosphonate or phosphonamidate linkage or a statine moiety incorporated at key sites in the amino acid sequence. These surrogate peptides were used to induce highly specific antibody combining sites designed to stabilize the energetically unfavorable, rate-limiting, tetrahedral intermediate for peptide hydrolysis.

The structures shown in FIG. 10 represent the putative transition for peptide hydrolysis by zinc peptidases and the phosphonate and phosphonamidate mimics. Similar tetrahedral transition state intermediates are formed in each of the four classes of proteolytic enzymes, the serine-, cysteine-, aspartic- and metallo-peptidases.

Figure 11:
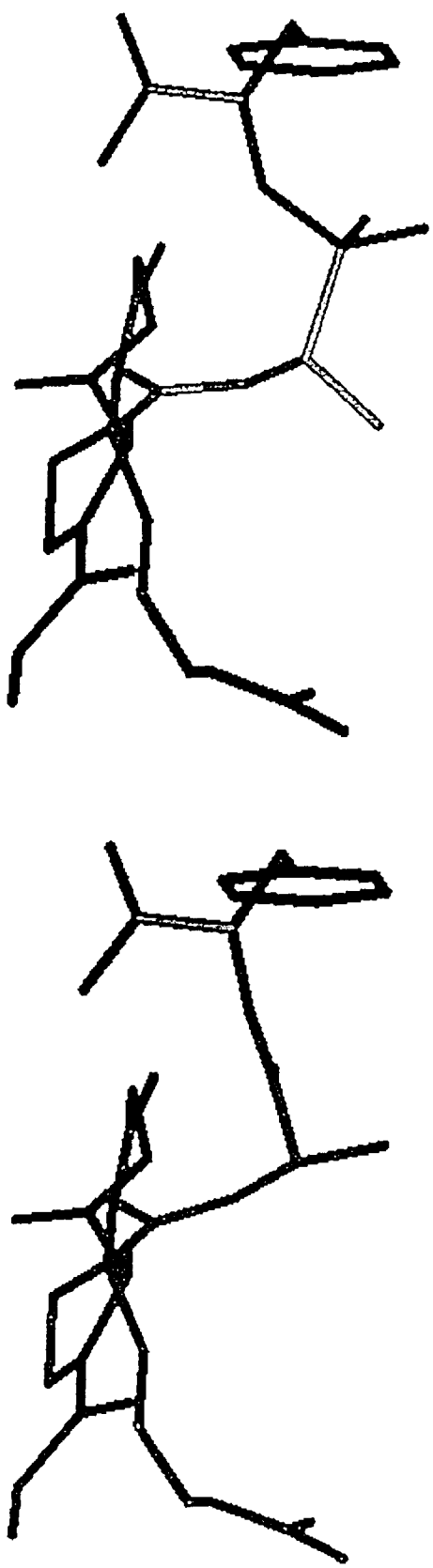
FIG. 11 Structural comparison of the HIV peptide Gly-Pro-Gly-Arg-Ala-CO-NH-Phe (SEQ ID NO: 1) (left) and its transition state analog Gly-Pro-Gly-Arg-Ala-$PO_2^-$—O—Phe (SEQ ID NO: 1)(right).
Figure 12:
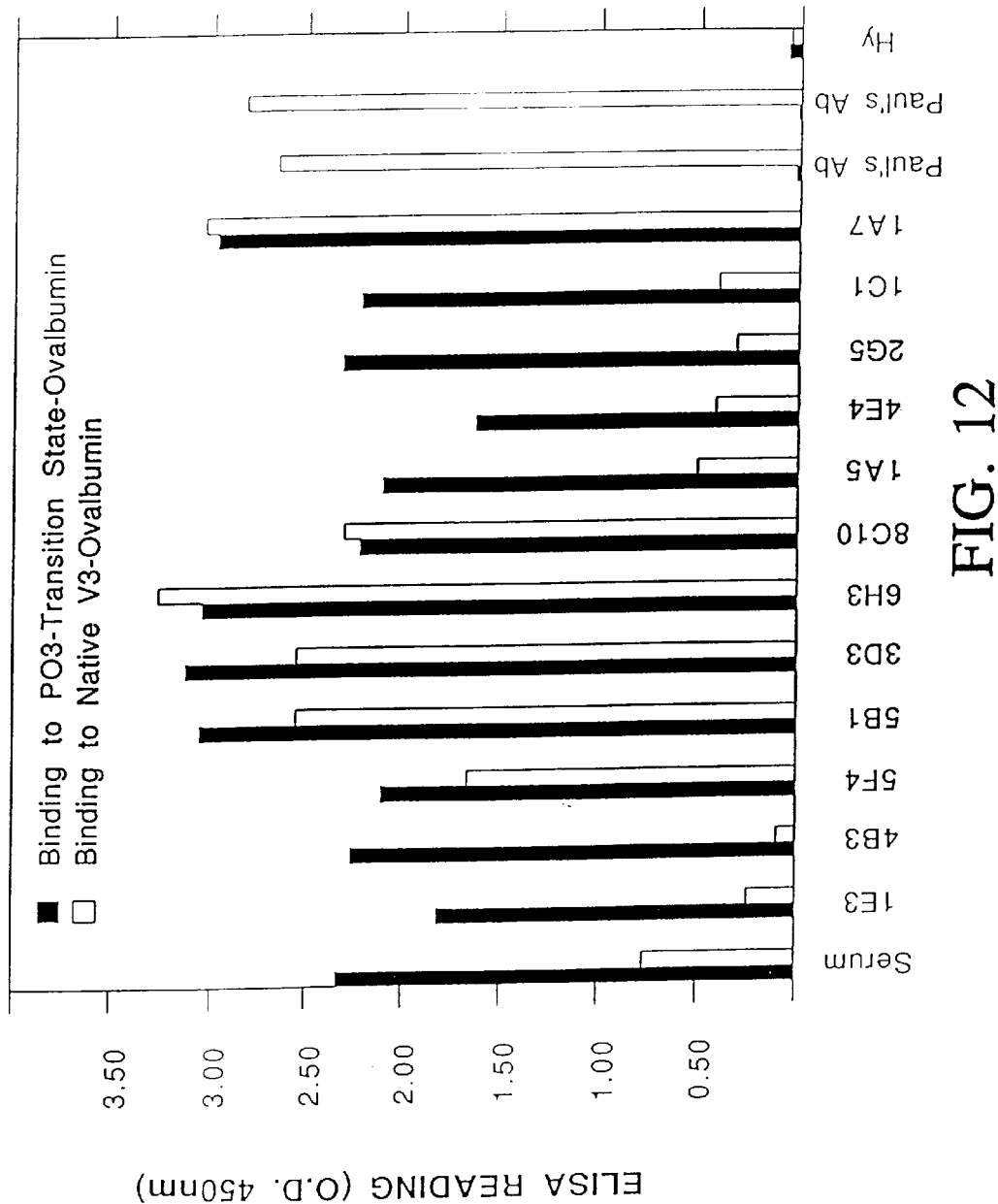
FIG. 12 HIV V3 peptide comparative ELISA.
Figure 13:
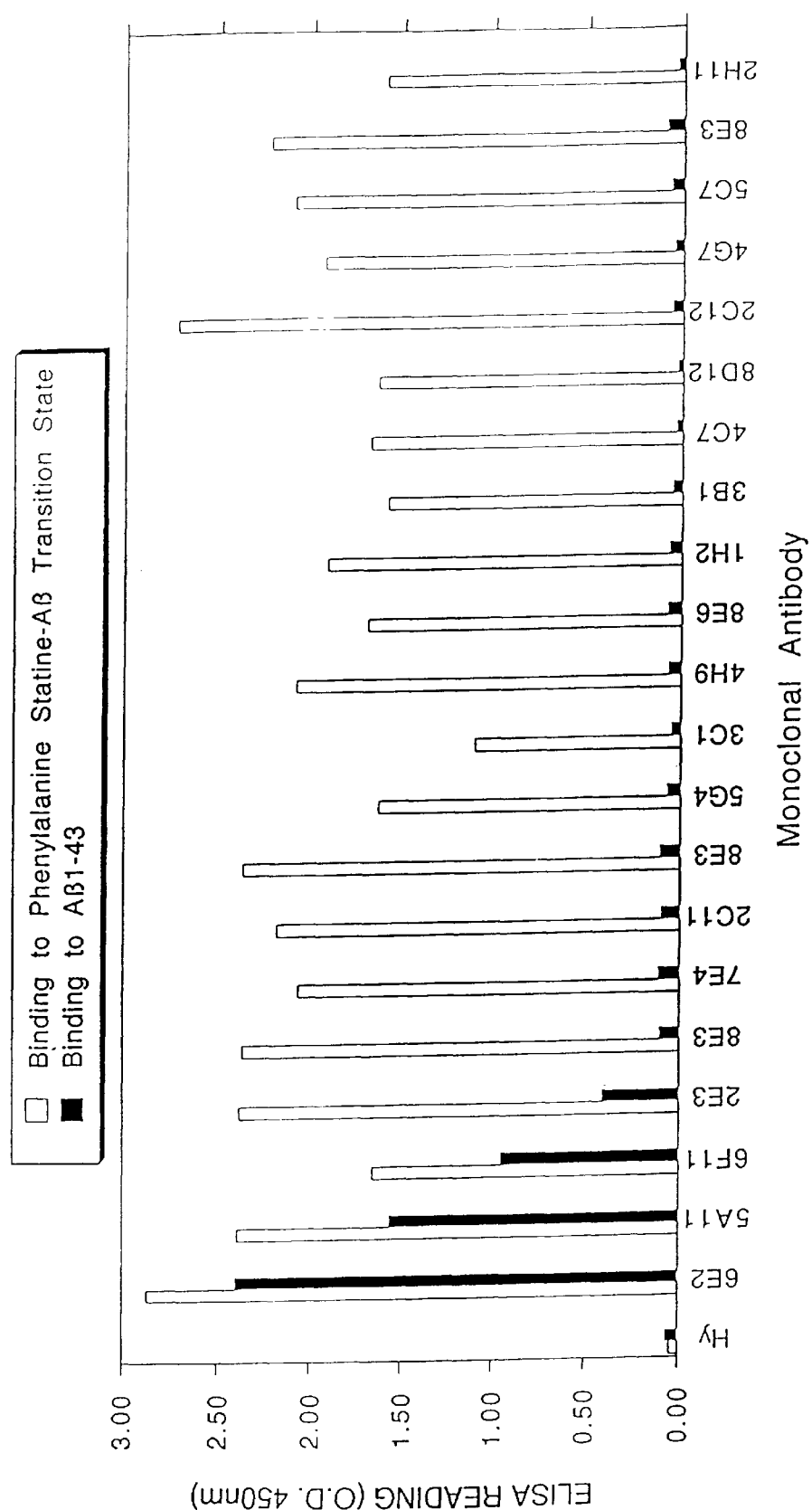
FIG. 13 Alzheimer's β-amyloid peptide comparative ELISA.
Figure 14:
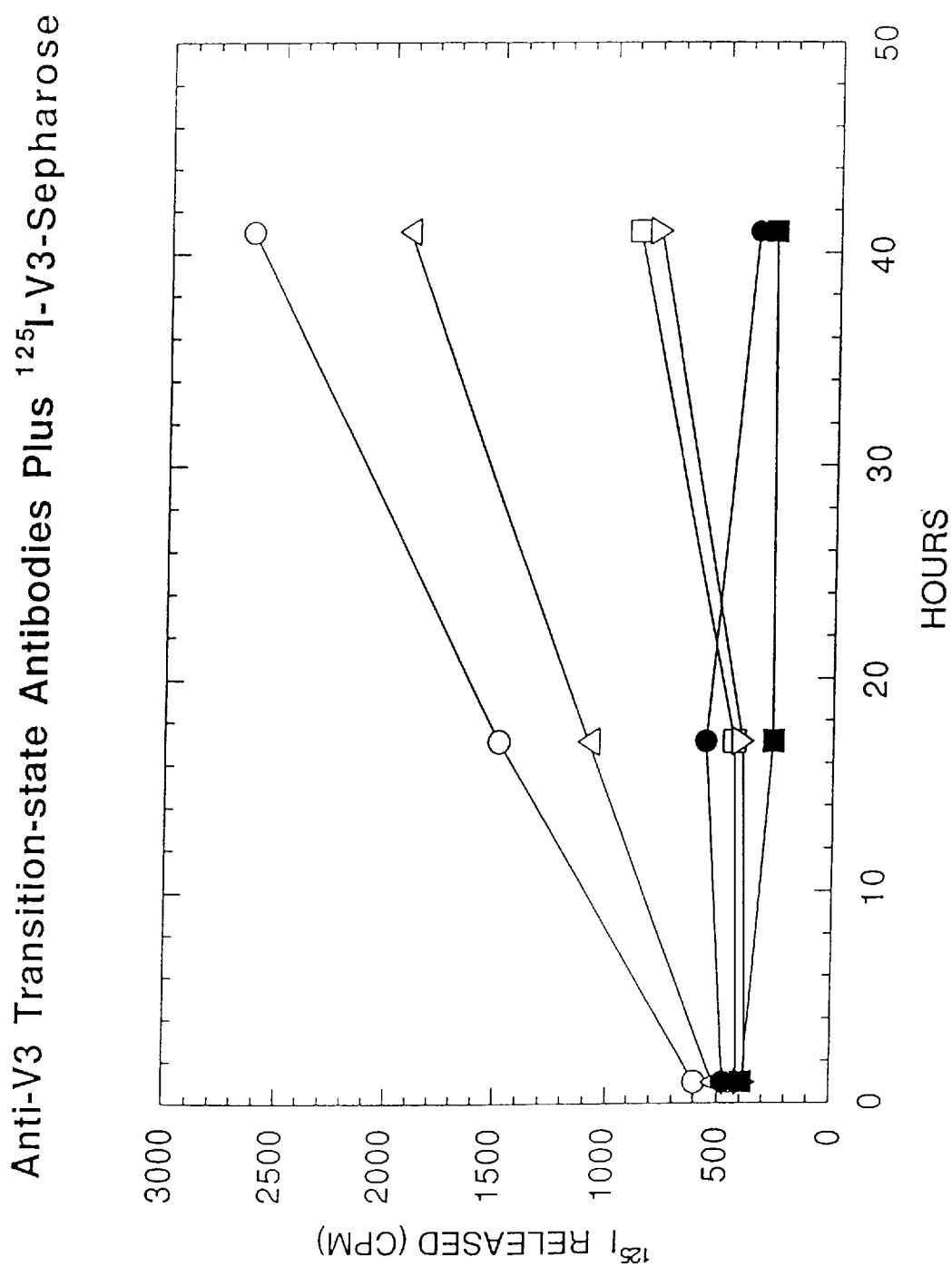
FIG. 14 Cleavage of solid phase $^{125}$I-V3 peptide.
Figure 15:
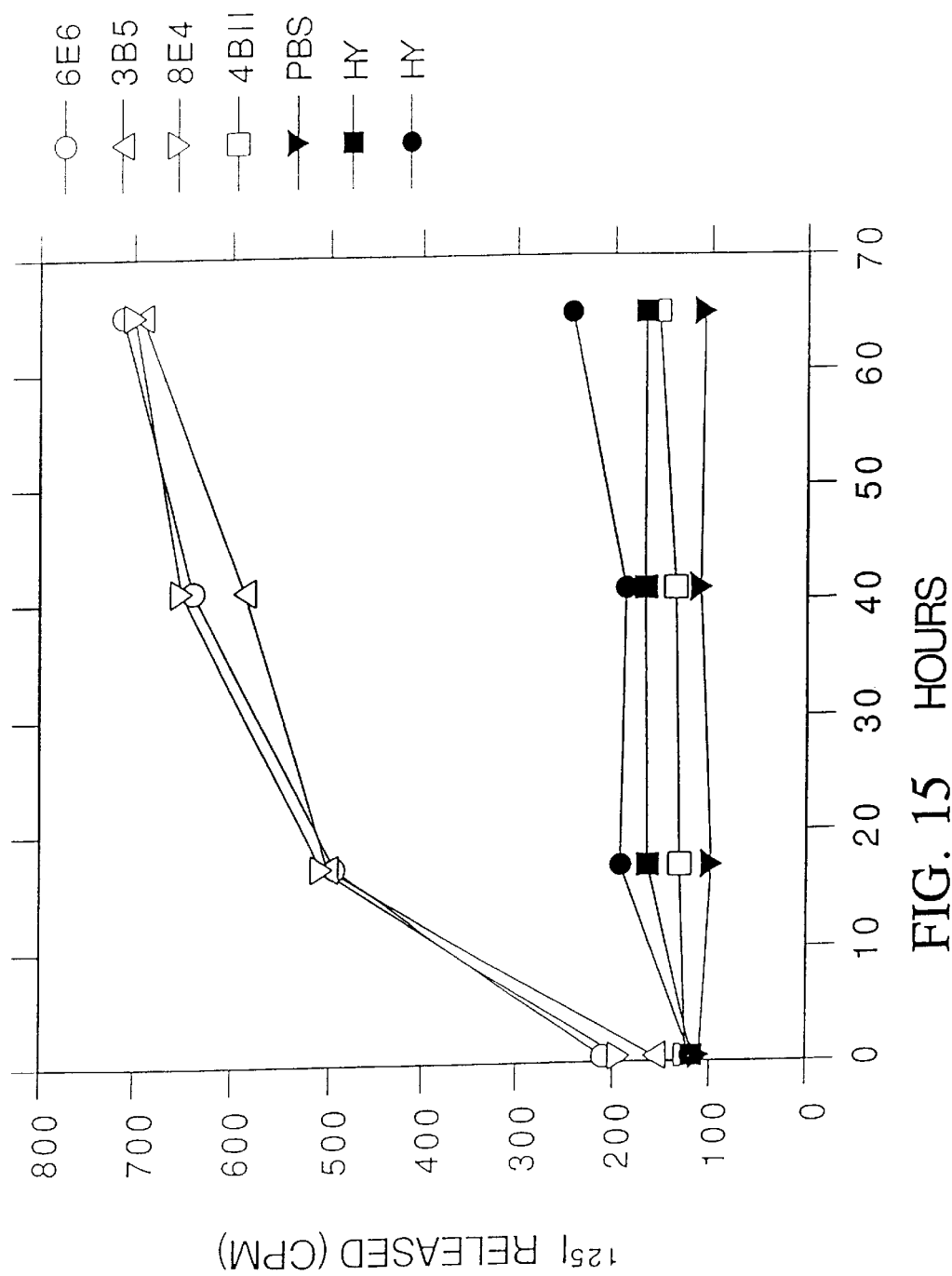
FIG. 15 Cleavage of solid phase $^{125}$I-β-amyloid peptide.

For example, a phosphonate transition state analog encompassing the crown of the HIV V3 loop (Gly-Pro-Gly-Arg-Ala-Phe SEQ ID NO: 1) was synthesized in this laboratory. Replacement of the proposed scissile peptide linkage between $Ala_{323}$ and $Phe_{324}$ with a phosphonate moiety ($—PO_2^-—O—$) (FIG. 11) was designed to elicit catalytic antibodies that will hydrolytically cleave the virus at this site in the V3 loop. A structural comparison was made between the native V3 crown peptide and the transition state peptide using a Silicon Graphics Iris Indigo XS24 graphics workstation (FIG. 11). Coordinates for the conformation of the natural V3 peptide as it resides in a monoclonal antibody combining site were obtained from published x-ray diffraction data (Ghiara et al., *Science* 264: 82–85 (1994)) deposited in the Brookhaven Protein Data Bank.

The peptide link —CO—NH— (↑) between $Ala_{323}$ and $Phe_{324}$ was replaced with a phosphonate bond $—PO_2^-—O—$ (↑). After tethering key atoms on either side of the modification to their starting conformation, an energy minimization was applied. The orientation shown in FIG. 11, clearly illustrates the difference between the planar peptide link —CO—NH— (↑) of native V3 on the left versus the corresponding tetrahedral phosphonate bond $—PO_2^-—O—$ (↑) in the transition-state peptide on the right.

A hybridoma fusion was performed using the spleen of a mouse immunized with the phosphonate transition state peptide-KLH antigen. Monoclonal antibodies from several of the hundreds of hybridoma supernatants produced were screened using ELISA to assess their binding to both normal V3 peptide and the phosphonate transition state V3 peptide. Data shown in FIG. 12 indicate that two patterns are discernable.

One group of antibodies bound equally well to both the immunizing transition-state peptide and the native V3 peptide when each was attached to ovalbumin. The second group showed a consistent preference for the phosphonate transition-state V3 peptide and reflected the specificity ratio found in the immune serum. Several clones, 2G5, 1C1, 1E3 and especially 4B3, displayed a pronounced binding preference for the transition-state peptide compared to the other antibodies assayed (FIG. 12).

The sample run in duplicate, labeled Paul's Ab, is a monoclonal antibody raised against the native V3 peptide and is reactive primarily with the GPGRAF crown epitope (Langedijk et al., *J. Gen. Virol.* 72: 2519–2526 (1991)). As expected, this antibody did not cross-react with the sterochemically altered transition state GPGRA-$PO_2^-$—O—F (SEQ ID NO: 1) peptide, but showed very strong binding to normal V3. Collectively, these findings indicate that the new anti-V3 transition-state antibodies are unique. They can recognize both the phosphonate- and normal-V3 peptides. Their unique cross-reaction with native V3, however, implies that this binding interaction is very different from that shown by conventional anti-native V3 antibodies. It suggests further that these new antibodies may be able to force the native V3 peptide into a conformation resembling the transition state for hydrolytic cleavage.

In another example, a phenylalanine statine (PhSta) transition state analog encompassing the central region of the 43 residue Alzheimer's β-amyloid peptide, $Aβ_{1-43}$, was synthesized using FMOC chemistry in this laboratory, (Cys-Tyr-Glu-Val-His-His-Gln-Lys-Leu-Val-PhSta-Phe-Ala-Glu-Asp-Val-Gly-amide SEQ ID NO: 2). Replacement of the proposed scissile peptide linkage between $Phe_{19}$ and $Phe_{20}$ with a statyl moiety ($—CHOH—CH_2—CO—NH—$) is designed to elicit catalytic antibodies that will hydrolytically cleave the Alzheimer's β-amyloid peptide at this site. A Cys residue was placed at the position of $Gly_9$ to provide a sulfhydryl linkage group for coupling the peptide to the maleimide-activated KLH antigenic carrier protein.

A hybridoma fusion was performed using mouse myeloma NS-1 cells and the spleen of a mouse immunized with the phenylalanine statine transition state Aβ-KLH antigen. Monoclonal antibodies from several of the hundreds of hybridoma supernatants produced were screened using ELISA to assess their binding to both the normal $Aβ_{1-43}$ peptide and to the phenylalanine statine transition state Aβ peptide. Two patterns were found (FIG. 13).

One group of antibodies (at the left of FIG. 13) bound to the immunizing transition state peptide and cross-reacted strongly with the native $Aβ_{1-43}$ peptide when each was adsorbed directly onto the ELISA plate. The second group (at the right) showed a high binding preference for the phenylalanine statine transition state Aβ peptide and reacted minimally with native $Aβ_{1-43}$.

These findings indicate that several of the new anti-Aβ transition state antibodies are unique. They can bind to both the phenylalanine statine- and normal-Aβ peptides. Their selective recognition of the transition state and weaker cross-reaction with native $Aβ_{1-43}$ however implies that this binding interaction is very different from that shown by conventional anti-native Aβ antibodies. It suggests further that these new antibodies may be able to force the native Aβ peptide into a conformation resembling the transition state for hydrolytic cleavage.

Additional distinct HIV and Alzheimer's β-amyloid peptide transition state analogs have been synthesized and the corresponding hybridoma fusions have been performed along similar lines as described above. Highly sensitive and specific proteolytic assays based upon the cleavage of solid phase $^{125}I$-peptides have been devised. Using those assays, the many different monoclonal antibodies that have been generated for the appropriate catalytic activity on the native HIV (FIG. 14) and β-amyloid peptide targets (FIG. 15) are currently being examined.

The results obtained at pH7, 25° C. indicate that the antibody-containing media of several anti-V3 transition state and anti-β-amyloid clones released $^{125}I$-peptide from their respective solid phase substrates at a greater rate than other clones from the fusions or the PBS, SHAM, and Hy medium controls. These antibodies will now be purified and tested a higher concentrations to obtain much higher rates of cleavage and to verify that the antibodies can be used as a starting point for generating anti-idiotypes and second generation catalytic antibodies.

Example 2

Production of Anti-idiotypic Antibodies

Mice have been immunized i.p. with complete Freunds adjuvant containing either purified whole MOPC 167 or MOPC 167 Fab fragments linked to KLH. Three days following a booster injection with antigen in PBS, the immune spleenocytes were used to perform a hybridoma fusion and antibody-producing clones were established. Additional immunizations and hybridoma fusions will be performed in a similar manner as new catalytic antibodies become available.

Hybridoma supernatants from the fusion detailed above were analyzed for MOPC 167 specific anti-idiotype antibodies with a dual ELISA (FIG. 16). They were first tested for reactivity with MOPC 167 Fab adsorbed directly on to the ELISA wells. A γ-specific anti-mouse IgG reagent was used for detection since it did not interact with the MOPC 167 IgA adsorbed to the wells. This first assay detects anti-idiotype antibodies reactive with the combining site of MOPC 167 (FIG. 16) as well as antibodies that interact at other sites on the Fab fragment. The latter, undesirable antibodies, were then identified by their reaction in a second ELISA that used MOPC 315 adsorbed to the microtitre wells. MOPC 315 is a class- and light chain-matched IgAλ myeloma protein that binds dinitrophenol and has no catalytic activity like that shown by MOPC 167. Only clones that were positive in the first ELISA and negative in the second were considered specific for the phosphocholine combining site and evaluated further. Several anti-idiotype antibodies have been identified by this technique and an example of the results obtained with one of these monoclonal anti-idiotype antibodies, 4G4, is shown in Table I.

TABLE I

Dual ELISA to Detect Anti-Idiotype Antibodies

| Addition | Antigen | Antibody Bound (O.D. 450 nm) |
| --- | --- | --- |
| No antibody | MOPC 167 | 0.163 |
| anti-Id 4G4 | MOPC 167 | 2.321 |
| No antibody | MOPC 315 | 0.238 |
| anti-Id 4G4 | MOPC 315 | 0.304 |

Two separate ELISAs were designed to unequivocally confirm that the anti-idiotype antibodies recognize the catalytic antibody combining site. Both are based on the competition between an anti-idiotype antibody and the transition state analog for binding to the catalytic active site (FIGS. 2 and 3).

The first competitive ELISA uses the MOPC 167 catalytic antibody adsorbed onto microtitre plate wells. This assay measures the blocking effect of the p-nitrophenylphosphorylcholine transition state analog on the binding of anti-idiotype antibodies to MOPC 167 (FIG. 2, A versus B).

A true combining site-reactive anti-idiotype antibody will be prevented from interacting with MOPC 167 if this assay is performed in the presence of an excess of the transition state analog because that analog will preoccupy the catalytic combining site (FIG. 2, B). Since the anti-idiotype is blocked from attaching to MOPC 167 and will subsequently wash away, a reduced signal is obtained after the peroxidase-labeled, γ-specific anti-mouse IgG reagent and its substrate are added (compare FIG. 2, A, unblocked control and B, transition state analog blockade).

The results in Table II show that this assay functions as predicted and also indicate that the monoclonal anti-idiotype antibodies designated 4G4 and 1F1 are directed against the MOPC 167 catalytic site. Binding of 4G4 and 1F1 to MOPC 167 was inhibited by 67% and 70% respectively when 10 mM p-nitrophenylphosphorylcholine TS analog was present. This incomplete blockage suggests that these bivalent anti-idiotype antibodies bind to the active site of MOPC 167 with much greater avidity then the small transition state analog which has an affinity of Ka ~$10^6$ M$^{-1}$ (Pollack et al., Science 234: 1570–1573 (1986)).

TABLE II

Competitive ELISA using the Free Transition State Analog

| Addition | Antibody Bound (O.D. 450 nm) |
| --- | --- |
| No antibody | 0.225 |
| No antibody + p-nitro TS analog | 0.245 |

TABLE II-continued

Competitive ELISA using the Free Transition State Analog

| Addition | Antibody Bound (O.D. 450 nm) |
| --- | --- |
| anti-Id 4G4 | 3.397 |
| anti-Id 4G4 + p-nitro TS analog | 1.113 |
| anti-Id 1F1 | 2.034 |
| anti-Id 1F1 + p-nitro TS analog | 0.769 |

The second competitive ELISA measures the interaction of MOPC 167, an anti-transition state antibody (anti-TS) with its conjugated transition state analog, diazophenylphosphorylcholine-BSA adsorbed onto microtitre plate wells (FIG. 3, A).

Binding of MOPC 167 to the immobilized transition state analog will be prevented if this assay is performed in the presence of a true combining site-reactive anti-idiotype (FIG. 3, B). Since the blocked MOPC 167 will subsequently wash away, a reduced signal is obtained after the peroxidase-labeled anti-mouse IgA reagent and its substate are added (compare FIG. 3, A, unblocked control and B, anti-idiotype blockade).

The results in Table III show that this assay functions as diagramed in FIG. 3. The binding of two concentrations of MOPC 167 to the immobilized transition state analog was competitively inhibited by 70% and 99% when the 4G4 anti-idiotype monoclonal antibody was included. These data reinforce the conclusion that this 4G4 antibody is indeed an internal image anti-idiotype directed against the MOPC 167 catalytic site.

TABLE III

ELISA using an Anti-Idiotype for Competition

| Addition | Antibody Bound (O.D. 450 nm) |
| --- | --- |
| No antibody | 0.051 |
| MOPC 167 | 1.800 |
| MOPC 167 + anti-Id 4G4 | 0.531 |
| MOPC 167 (1/10) | 1.587 |
| MOPC 167 (1/10) + anti-Id 4G4 | 0.069 |

A related method for detecting the interaction of the anti-idiotype antibodies with the catalytic site of MOPC 167 is to measure the blockage of its catalytic activity. MOPC 167 catalysis can be assayed by monitoring p-nitrophenol production at 400 nm (FIG. 4) as previously reported (Pollack et al., Science 234: 1570–1573 (1986)) or by thiocholine production at 412 nm (FIG. 5) (Raso, V., unpublished results). When these assays are run in the presence of a catalytic site-specific anti-idiotype, access of the substrate will be prevented and the rate of hydrolysis should be accordingly reduced. If this spectrophotometric method is used to assay antibodies in hybridoma supernatants, phenol red-free media will be used or the anti-idiotype antibodies can be purified to avoid interference from any colored species.

Example 3

Production of Second Generation Anti-Anti-Idiotype Catalytic Antibodies

Anti-MOPC 167 idiotypic antibody 4G4 has been isolated from ascites fluid by protein A affinity chromatography. Fab fragments were prepared by enzymatic digestion and then purified. Mice have been immunized i.p. with complete Freunds adjuvant containing either purified whole 4G4 anti-MOPC 167 idiotype antibody or 4G4 anti-MOPC 167 idiotypic antibody Fab fragments linked to KLH. Three days following a booster injection with antigen in PBS, the immune spleenocytes will be used to perform a hybridoma fusion and antibody-producing clones will be established. Additional immunizations and hybridoma fusions will be performed in a similar manner as new anti-idiotypic antibodies become available for this project.

The hybridoma supernatants from the fusion detailed above, can be analyzed for specific anti-anti-idiotype antibody binding and will be compared with binding to a class-matched control antibody. A peroxidase-labeled anti-Fc reagent will be used since this can detect the bound anti-anti-idiotype antibody, but will not interact with the anti-idiotype Fab already on the plate.

While the dual ELISA is one way to identify anti-anti-idiotype antibodies, a much simpler and more direct ELISA would measure binding to the original transition state analog. This follows when one considers that these anti-anti-idiotype antibodies are the equivalent of an anti-transition state catalytic antibody as shown by the diagram in FIG. 1.

Therefore, sera and monoclonal antibodies obtained from these mice will be quickly screened for anti-anti-idiotype antibodies by a combining site-specific ELISA. It uses the transition state analog diazophenylphosphorylcholine-BSA conjugate adsorbed to microtitre wells and a perioxidase-labeled anti-mouse IgG specific detection reagent (FIG. 17).

Isolation of the anti-anti-idiotype antibodies from hybridoma cell culture medium or from the ascites fluid of pristane-primed mice inoculated with hybridoma cells can be accomplished by two simple methods. Standard purification could be carried out on a protein A Sepharose column. However, the antibody can also be isolated by affinity chromatography using the same Sepharose-immobilized p-aminophenylyphosphorylcholine transition state analog (Chesebro and Metzger, *Biochemistry* 11: 766–771 (1972)) that was used to purify MOPC 167.

With purified anti-anti-idiotype antibodies in hand, their binding specificity and the mechanism of antibody-dependent catalysis will be characterized. Direct binding of $^{125}$I-p-hyroxyphenylphosphorylcholine to the antibodies will be measured by equilibrium dialysis or by polyethylene glycol precipitation methods. This will provide a quantitative measure of affinity that will augment the specificity data obtained by ELISA.

The assay and conditions described for the measurement of MOPC 167 catalysis (FIGS. 4 and 5 and (Pollack et al., *Science* 234: 1570–1573 (1986)) will be used for measuring the catalytic activity of the anti-anti-idiotype antibodies. As noted, a comparison will be made with the uncatalyzed reaction run under identical conditions. At this stage, however, some very important controls will be run. First, it will ensured that catalytic antibody activity is completely blocked by the p-nitrophenylphosphorylcholine transition state and thereby prevent substrate binding or hydrolysis (FIG. 8). Substrate specificity will be further established by showing less cleavage of substrate analogs (Pollack et al., *Science* 234: 1570–1573 (1986)). The products of hydrolysis will be fully characterized by HPLC, amino acid and mass spectral analysis. Control antibodies will be tested and are expected to produce no catalysis. Moreover, catalytic activity will be shown to reside in the purified Fab fragments of the anti-anti-idiotype antibodies.

A kinetic analysis of the antibody catalyzed reaction will be performed as shown in FIGS. 6 and 7, by measuring the initial rates of hydrolysis as a function of substrate concentration. Data will be analyzed on a Lineweaver-Burke plot so that it can be confirmed that the reaction follows classical Michaelis-Menten kinetics. A rate acceleration for hydrolysis will be calculated by the ratio of $k_{cat}/k_{uncat}$. The reaction will also be allowed to proceed for an extended length of time to demonstrate catalytic turnover. These purified anti-anti-idiotype antibodies will be compared with the original MOPC 167 catalytic antibody to directly evaluate their relative catalytic effectiveness.

Example 4

Proposed Studies

The studies outlined above focus on obtaining proof of concept data which will support the idea of using idiotypic mimicry to create novel anti-idiotype vaccines for generating improved catalytic antibodies. Hence these initial experiments are designed to replicate catalytic antibodies with a simple esterase activity that is easily measured. Additional work however is directed toward producing clinically useful anti-idiotype vaccines and catalytic antibodies. Preliminary work on generating catalytic antibodies for sequence-specific proteolytic cleavage of the HIV gp120 envelope protein or the Alzheimer's β-amyloid peptide has already been presented. Anti-idiotype vaccines that elicit catalytic antibodies which selectively destroy such relevant target molecules may have a direct bearing upon the treatment or prevention of human disease.

Another potential area where catalytic antibody-inducing anti-idiotype vaccines should be useful is in the treatment of human addiction. For example, catalytic antibodies that hydrolytically inactivate cocaine have been produced and their use for intervention in cocaine dependence by passive administration has been suggested (Landry et al., *Science* 259: 1899–1901 (1993)). Clearly, these mouse antibodies could not be injected to deplete cocaine after each usage of the drug by an addict, especially given the danger of anaphylactic shock. However, if the patient were voluntarily immunized and boosted with an anti-idiotype against these catalytic antibodies, they would continuously produce high levels of endogenous catalytic antibodies. Cocaine would rapidly be eliminated after each use and substance abuse would therefore not be reinforced. Methods of this invention to be employed are outlined below.

PRODUCTION OF FIRST GENERATION ANTI-COCAINE CATALYTIC ANTIBODIES

Generation of Primary Anti-Cocaine Monoclonal Catalytic Antibodies

Primary anti-cocaine monoclonal catalytic antibodies will be generated using the phosphonate cocaine transition state analog linked to a KLH carrier protein, as previously reported (Yang et al., *Journal of the American Chemical Society* 118: 5881 (1996), Landry et al., *Science* 259: 1899 (1993)). This antigen will be used to immunize mice. Hybridoma clones will be established and these will be screened for the presence of anti-cocaine transition state analog antibodies by ELISA. Those antibodies which are positive will be purified using protein A and then analyzed for catalytic activity (Yang et al., *Journal of the American Chemical Society* 118: 5881 (1996), Landry et al., *Science* 259: 1899 (1993)). This will be accomplished using commercially available levo-[benzoyl-3,4-$^3$H]-cocaine and extraction of the cleaved benzoic acid into an organic solvent (Yang et al., *Journal of the American Chemical Society* 118: 5881 (1996), Landry et al., *Science* 259: 1899 (1993)). A comparison will be made to the uncatalyzed reaction run under identical conditions.

Induction of Anti-Idiotype Antibodies

Several of the best hybridoma clones obtained from the above procedure will be used to immunize pristane-primed mice. The mice will be tapped so that the catalytic monoclonal antibodies can be isolated from the ascites fluid by protein A affinity chromatography. The purified anti-cocaine catalytic antibodies and their Fab fragments will be prepared and linked to a KLH carrier protein. Those conjugates will be used as antigens to immunize mice and elicit anti-idiotype antibodies. The immunized mice will be monitored periodically for the production of an immune response to the antigen. At that point they will be used to generate hybridoma clones producing anti-idiotype antibodies. Those new anti-idiotypic antibodies will complement the binding site of the anti-cocaine catalytic antibody and mimic the true transition state for cocaine hydrolysis.

MOPC 167 is the prototype that we first tried for generating anti-idiotype antibodies reactive with a catalytic combining site. A similar immunization protocol will be used for generating anti-idiotypes against the new anti-cocaine catalytic antibodies. Therefore we anticipate that anti-idiotypic antibodies against the cocaine catalytic site will also be obtained in a straightforward manner.

Screen for Monoclonal Anti-Idiotype Antibodies

A dual ELISA system that detects binding to the anti-cocaine catalytic antibody versus a class- and light chain-matched normal antibody will be used to detect anti-idiotype antibodies in the hybridoma supernatants. The problem of cross-reactivity of the peroxidase-labeled detection reagent will be overcome by using Fab fragment of the anti-cocaine catalytic antibody adsorbed to the ELISA plate. The "whole" monoclonal anti-idiotype antibodies which bind to these Fab fragments will then be selectively revealed using a peroxidase-labeled anti-mouse Fc-specific probe (FIG. 16).

The selected anti-idiotype antibodies will be subsequently tested for recognition of the cocaine catalytic antibody combining site by blockage of catalytic activity or by its competition with the cocaine transition state analog for binding to the active site. The bases for these competition assays have already been established for the MOPC 167 prototype as previously described. Several combining site-specific anti-idiotype antibodies directed against the MOPC 167 catalytic antibody have been identified by these procedures (see the 4G4 and 1F1 anti-idiotype antibodies, Tables I, II and III). Anti-idiotype antibodies directed against the cocaine catalytic antibody active site will be similarly identified.

GENERATION OF ANTI-ANTI-IDIOTYPE ANTIBODIES WITH IMPROVED CATALYTIC PROPERTIES

Immunization with Anti-Idiotype Antibody

Several anti-cocaine idiotypic antibodies will be isolated from ascites fluid by protein A affinity chromatography. Fab fragments will be prepared by enzymatic digestion and then purified. Mice will be immunized inter-peritoneally with complete Freunds adjuvant containing either purified whole anti-cocaine idiotypic antibody or anti-cocaine idiotypic antibody Fab fragments linked to KLH (Chen et al., *Journal of Immunology* 147(3): 1082 (1991), Ferrone, S., *Hybridoma* 12(5): 509 (1993)). Sera from these animals will be tested by ELISA for the presence of anti-anti-idiotype antibodies and positive animals will be used as a source of spleen cells to generate hybridomas (Ferrone et al., *Journal of Dermatology* 20(9): 533 (1993)). Three days following a booster injection with antigen in PBS, the immune spleenocytes will be used to perform a hybridoma fusion and antibody-producing clones will be established.

Screen for Combining Site-Specific Anti-Anti-Idiotype Antibodies

The hybridoma supernatants from the fusions detailed above will be analyzed for specific anti-anti-idiotype antibodies with a dual ELISA similar to that shown in FIG. 16. The anti-cocaine idiotype Fab fragments will be adsorbed to the microtiter wells and anti-anti-idiotype antibody binding will be compared with binding to a class and light chain-matched control antibody. A peroxidase-labeled anti-mouse Fc reagent will be used since this will detect the bound "whole" anti-anti-idiotype antibody but will not interact with the anti-cocaine idiotype Fab fragments already on the plate. These anti-anti-idiotype antibodies are the equivalent of an anti-transition state catalytic antibody as shown by the diagram in FIG. 1. Therefore, sera and monoclonal antibodies obtained from these mice will be quickly screened for anti-anti-idiotype antibodies by a combining site-specific ELISA. This method uses the cocaine transition state analog-BSA conjugate adsorbed to microtitre wells and a peroxidase-labeled anti-mouse IgG specific detection reagent.

Examine Anti-Anti-Idiotypes For High Frequency and Improved Catalytic Activity

Isolation of the anti-anti-idiotype antibodies from hybridoma cell culture medium or from the ascites fluid of pristane-primed mice inoculated with hybridoma cells will be accomplished by one of two simple methods. Standard purification will be carried out on a protein A Sepharose column, or alternatively the antibody will be isolated by affinity chromatography using a Sepharose-immobilized cocaine phosphonate transition state analog.

With purified anti-anti-idiotype antibodies in hand, the binding specificity and the basic mechanism of antibody-dependent catalysis will be characterized. Direct binding of levo-[benzoyl-3,4-$^3$H]- cocaine to the antibodies will be measured by equilibrium dialysis or by polyethylene glycol precipitation methods. This will provide a quantitative measure of affinity that will augment the specificity data obtained by ELISA.

The assays and conditions described for the measurement of levo-[benzoyl-3,4-$^3$H]-cocaine hydrolysis by the primary anti-cocaine catalytic antibodies (Yang et al., *Journal of the American Chemical Society* 118: 5881 (1996), Landry et al., *Science* 259: 1899 (1993)) will also be used for measuring the catalytic activity of the anti-anti-idiotype antibodies. As noted, a comparison will be made with the uncatalyzed reaction run under identical conditions. At this stage, however, some very important controls will be run. First, the complete blockage of the catalytic antibody activity by the cocaine phosphonate transition state analog will be ensured. This non-cleavable "inhibitor" should bind much more tightly to the antibody combining sites and thereby prevent substrate binding or hydrolysis (FIGS. 6, 7). Substrate specificity will be further established by showing less cleavage of sterically altered cocaine analogs (Yang et al., *Journal of the American Chemical Society* 118: 5881 (1996), Landry et al., *Science* 259: 1899 (1993)). The products of hydrolysis will be fully characterized by HPLC, amino acid and mass spectral analysis. Control antibodies will be tested and are expected to produce no catalysis. Moreover, catalytic activity will be shown to reside in the purified Fab fragments of the anti-anti-idiotype antibodies. A kinetic analysis of the antibody catalyzed reaction will be performed as previously described, measuring the initial rates of hydrolysis as a function of substrate concentration. Data will be analyzed on a Lineweaver-Burke plot so that it can be confirmed that the reaction follows classical Michaelis-Menton kinetics. A rate acceleration for hydrolysis will be calculated by the ratio of $k_{cat}/k_{uncat}$. The reaction will also be allowed to proceed for an extended length of time to demonstrate catalytic turnover. These purified anti-anti-idiotype antibodies will be compared with the original anti-cocaine catalytic antibody to directly evaluate their relative catalytic effectiveness.

The question of frequency of catalytic antibody production is an important one (i.e. what is the ratio of the number of catalytic antibodies generated by an immunogen compared to the total number of anti-transition state analog antibodies produced?). Clearly, for therapeutic purposes it would be advantageous to induce a preponderance of active catalytic antibodies and fewer of the useless non-catalytic antibody species which might inhibit catalysis by competitively binding the substrate. Therefore, the frequency for obtaining monoclonal catalytic antibodies after immunizing with a conventional transition state analog antigen versus immunizing with the corresponding anti-idiotype antibody transition state mimic will be calculated and compared. This data should give us a rough estimate of which antigen will constitute the superior vaccine. If, as we have postulated, the anti-idiotype is a frozen image of the true transition state while the transition state analog only fleetingly represents that true transition state then the former should elicit a much higher frequency ratio of catalytic antibodies. To achieve this head-to-head comparison, a cocaine phosphonate transition state analog-KLH conjugate will be used to elicit monoclonal antibodies in mice as previously described. Another group of mice will be immunized with an anti-idiotype antibody directed against the combining site of one of the catalytic antibodies generated by that same cocaine transition state analog antigen. Hybridoma fusions will be performed and the number of anti-transition state analog antibodies generated by each group will be evaluated by an identical ELISA protocol. The resulting positive clones from each group will next be tested for catalytic activity according to established procedures. Lastly, the ratio of the number of anti-cocaine catalytic antibodies generated by the two different immunogens in comparison to the total number of anti-cocaine transition state analog antibodies produced by each will be calculated. We would predict that the anti-idiotype response should be enriched with catalytic antibodies compared to the anti-transition state response.

The above procedures are outlined with the primary goal of the production of clinically useful cocaine-specific anti-idiotype vaccines generating catalytic antibodies. Anti-idiotype vaccines will be effective for inducing anti-cocaine catalytic antibodies and should therefore be useful in the treatment of human addiction. For instance, catalytic antibodies that hydrolytically inactivate cocaine have been produced and their use for intervention in cocaine dependence by passive administration has been suggested (Landry et al., *Science* 259: 1899 (1993)). Clearly, these mouse antibodies could not be injected to deplete cocaine after each usage of the drug by an addict, especially given the danger of anaphylactic shock from the foreign protein. However, if the patient were voluntarily immunized and boosted with an anti-idiotype against the catalytic antibody they would continuously produce high levels of endogenous catalytic antibodies. Cocaine should rapidly be eliminated after each use and substance abuse would therefore not be reinforced. Animal models of cocaine self-administration (Pickens et al., *J. Pharm. and Experimental Therapeutics* 161: 122 (1968)) will be used to evaluate the effectiveness of this therapeutic idiotype vaccine.

The progress of catalytic antibody technology has been substantial since the original concept was envisioned and worked on many years ago (Raso and Stollar, *Biochemistry* 14: 591–599 (1975), Raso and Stollar, *J Amer Chem Soc* 95: 1621 (1973), Raso and Stollar, *Biochemistry* 14: 584–591 (1975)). The newly devised anti-idiotype strategy should take catalytic antibodies the next logical step forward by establishing them in the realm of medically useful therapeutic agents.

What is claimed is:

1. A method for generating second generation catalytic antibodies, comprising:
   a) immunizing a first animal with a transition state analog;
   b) producing hybridomas and screening for production of monoclonal antibodies specific for the transition state analog and having catalytic activity;
   c) immunizing a second animal with a monoclonal antibody identified in step b);
   d) producing hybridomas and screening for production of anti-idiotypic monoclonal antibodies having a structure which mimics the transition state analog; and
   e) immunizing a third animal with the anti-idiotypic monoclonal antibody of step d) to produce anti-anti-idiotypic antibodies having catalytic activity.

2. The method of claim 1 wherein the third animal is a human and the immunization is an active immunization.

3. The method of claim 1 wherein the transition state analog mimics the transition state adopted by the cocaine molecule during chemical hydrolysis.

4. A method for generating second generation catalytic antibodies, comprising:
   a) immunizing cultured spleen cells, in vitro, with a transition state analog;
   b) producing hybridomas and screening for production of monoclonal antibodies specific for the transition state analog and having catalytic activity;
   c) immunizing an animal with a monoclonal antibody identified in step b);
   d) producing hybridomas and screening for production of anti-idiotypic monoclonal antibodies having a structure which mimics the transition state analog; and
   e) immunizing a second animal with the anti-idiotypic monoclonal antibody of step d) to produce anti-anti-idiotypic antibodies having catalytic activity.

5. The method of claim 4 wherein the third animal is a human and the immunization is an active immunization.

6. The method of claim 4 wherein the transition state analog mimics the transition state adopted by the cocaine molecule during chemical hydrolysis.

7. A method for generating second generation catalytic antibodies, comprising:
   a) providing DNA from a naive animal, or an animal immunized with a transition state analog;
   b) preparing a phage display library;
   c) screening the phage display library with the transition state analog;
   d) expressing DNA from phage identified in screening step c) to produce monoclonal antibody fragments specific for the transition state analog;
   e) immunizing an animal with a monoclonal antibody fragment identified in step d);
   f) producing hybridomas and screening for production of anti-idiotypic monoclonal antibodies having a structure which mimics the transition state analog; and
   g) immunizing a second animal with the anti-idiotypic monoclonal antibody of step f) to produce anti-anti-idiotypic antibodies having catalytic activity.

8. The method of claim 7 wherein the third animal is a human and the immunization is an active immunization.

9. The method of claim 7 wherein the transition state analog mimics the transition state adopted by the cocaine molecule during chemical hydrolysis.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Human immunodeficiency virus

<400> SEQUENCE: 1

Gly Pro Gly Arg Ala Phe
 1               5

<210> SEQ ID NO 2
<211> LENGTH: 17
<212> TYPE: PRT
<213> ORGANISM: Homo sapiens
<220> FEATURE:
<223> OTHER INFORMATION: The transition state analog phenylalanine
      statine is located at the position designated Xaa  in the
      sequence listing.

<400> SEQUENCE: 2

Cys Tyr Glu Val His His Gln Lys Leu Val Xaa Phe Ala Glu Asp Val
 1               5                  10                  15

Gly
```